United States Patent [19]

Bullis

[11] Patent Number: 4,546,444
[45] Date of Patent: Oct. 8, 1985

[54] DATA COMPRESSION INTERFACE HAVING PARALLEL MEMORY ARCHITECTURE

[75] Inventor: David C. Bullis, Kennett Square, Pa.

[73] Assignee: E. I. Du Pont de Nemours and Company, Wilmington, Del.

[21] Appl. No.: 475,505

[22] Filed: Mar. 15, 1983

[51] Int. Cl.$^4$ ............................................. G01N 21/32
[52] U.S. Cl. .................................. 364/550; 364/469; 356/431; 250/563; 250/572
[58] Field of Search .......................... 364/550, 469–472; 356/429–431; 250/560–563, 571, 572

[56] References Cited

U.S. PATENT DOCUMENTS

| 3,898,469 | 8/1975 | Nichols et al. | 250/563 |
| 3,980,891 | 9/1976 | Slaker | 250/563 |
| 4,134,684 | 1/1979 | Jette | 356/430 |
| 4,173,441 | 11/1979 | Wolf | 356/431 |

Primary Examiner—Edward J. Wise
Attorney, Agent, or Firm—George M. Medwick

[57] ABSTRACT

A data compression interface is characterized by a memory system having an architecture configured from a first and a second serial memory connected in parallel. One memory serves during alternate frames as a data collection memory while the other serves during that same frame as an output memory.

27 Claims, 22 Drawing Figures

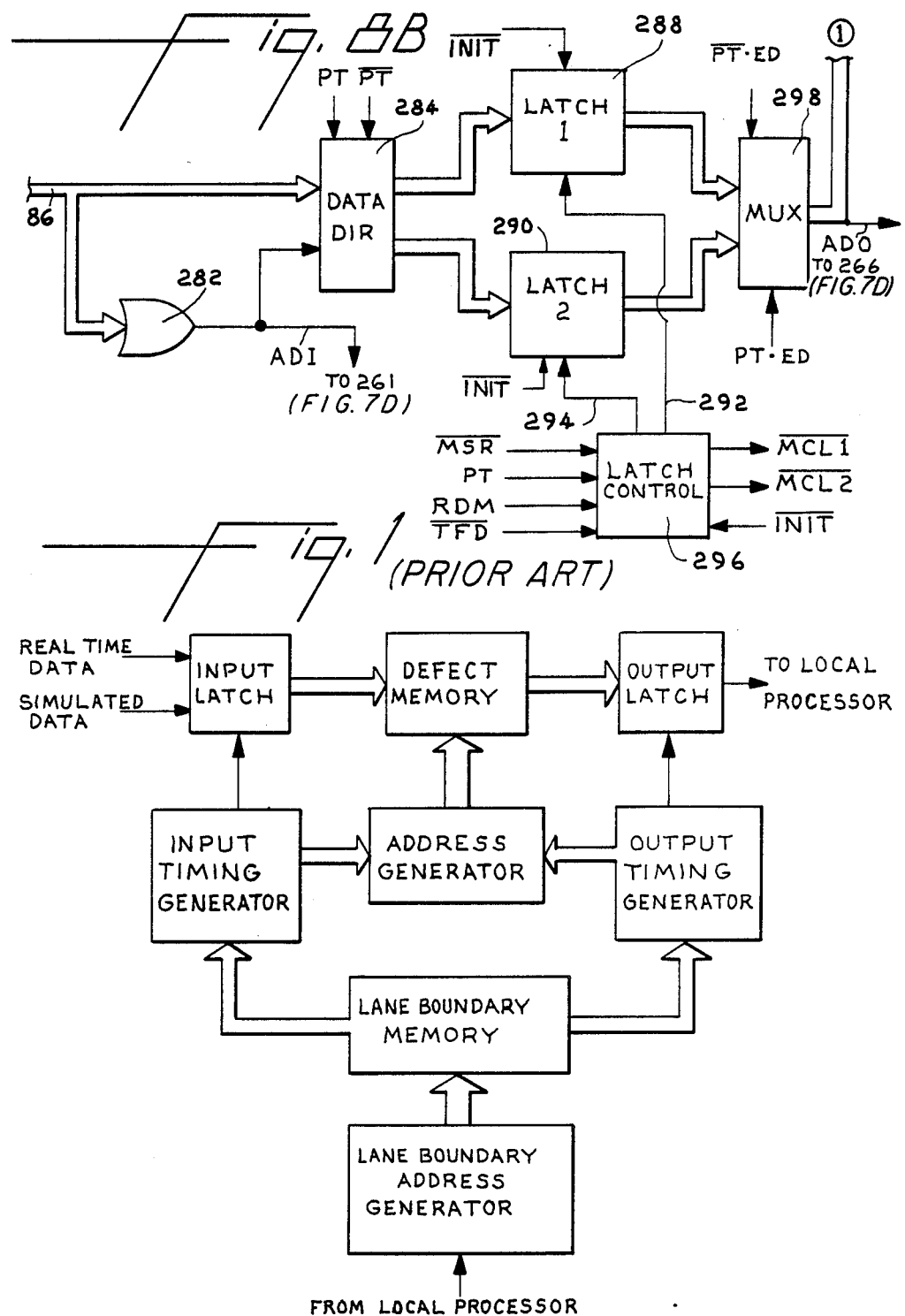

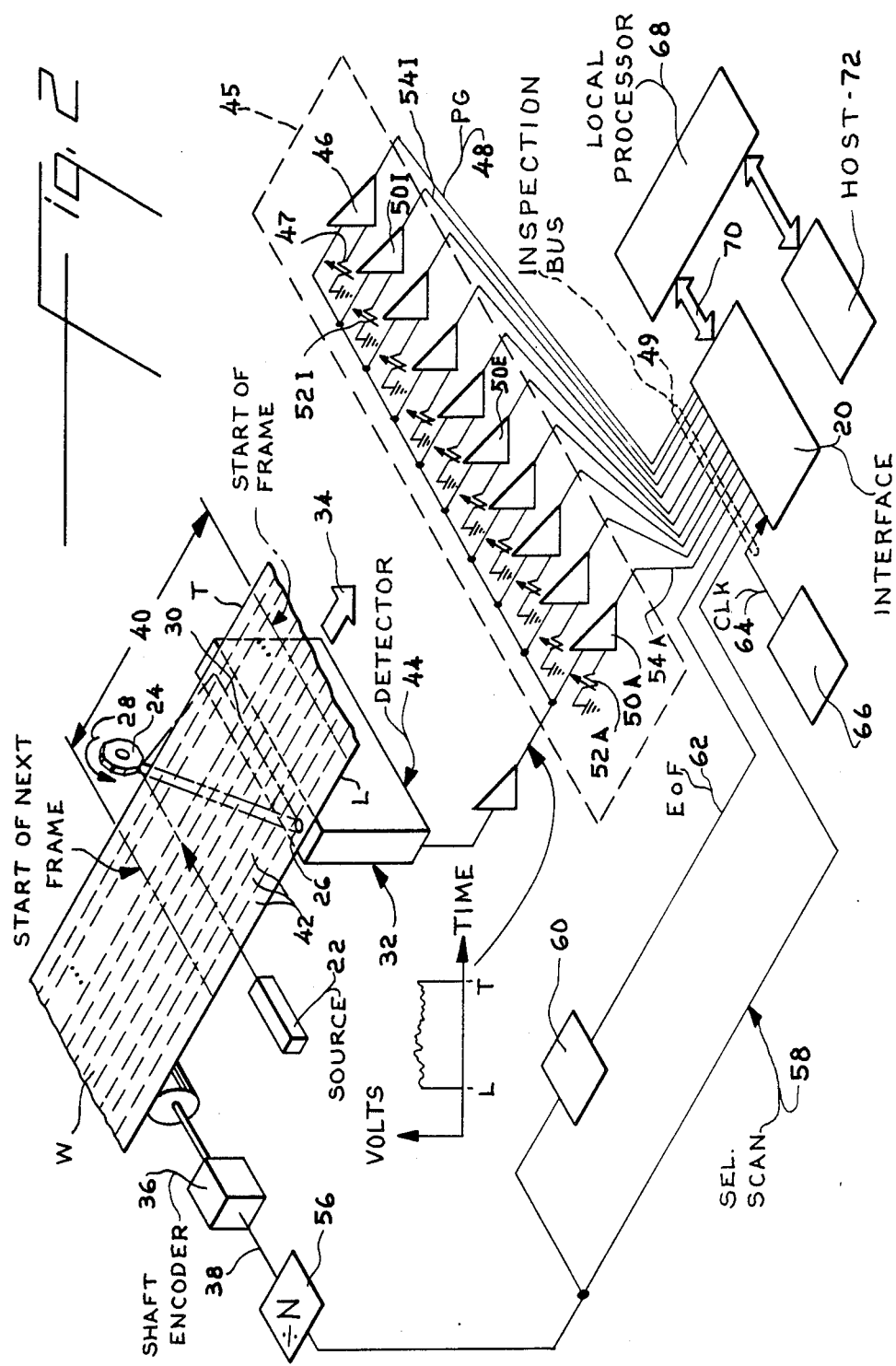

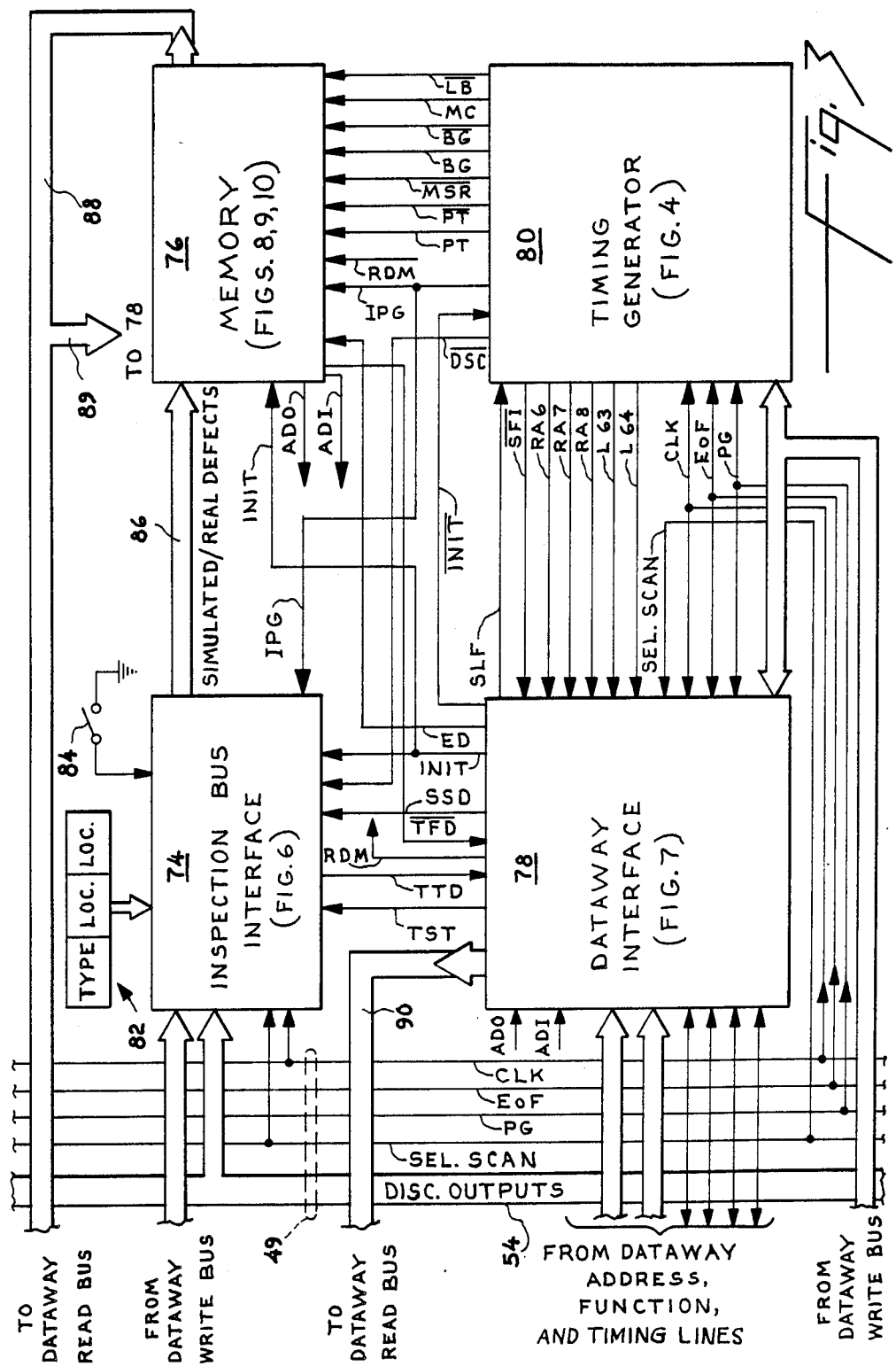

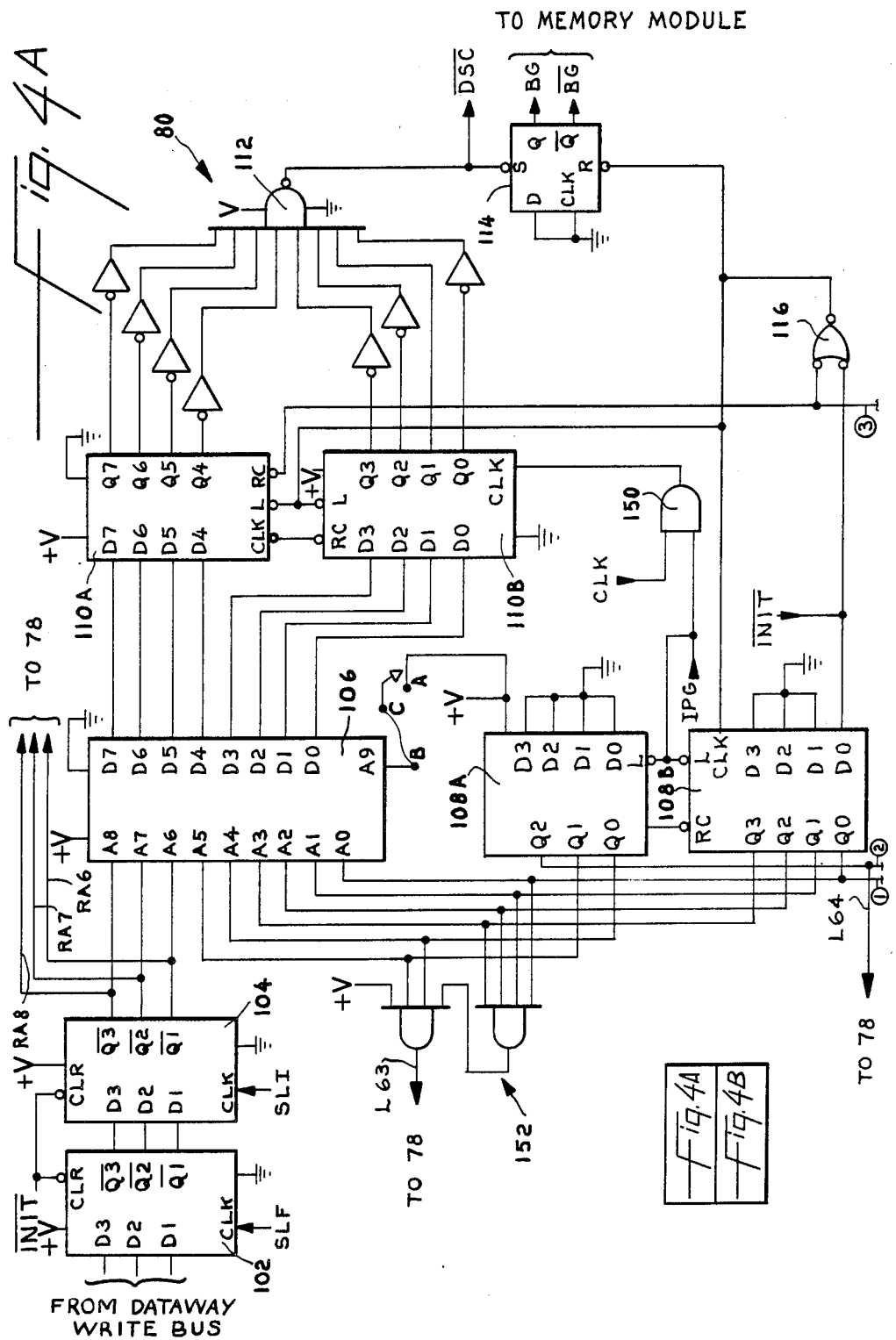

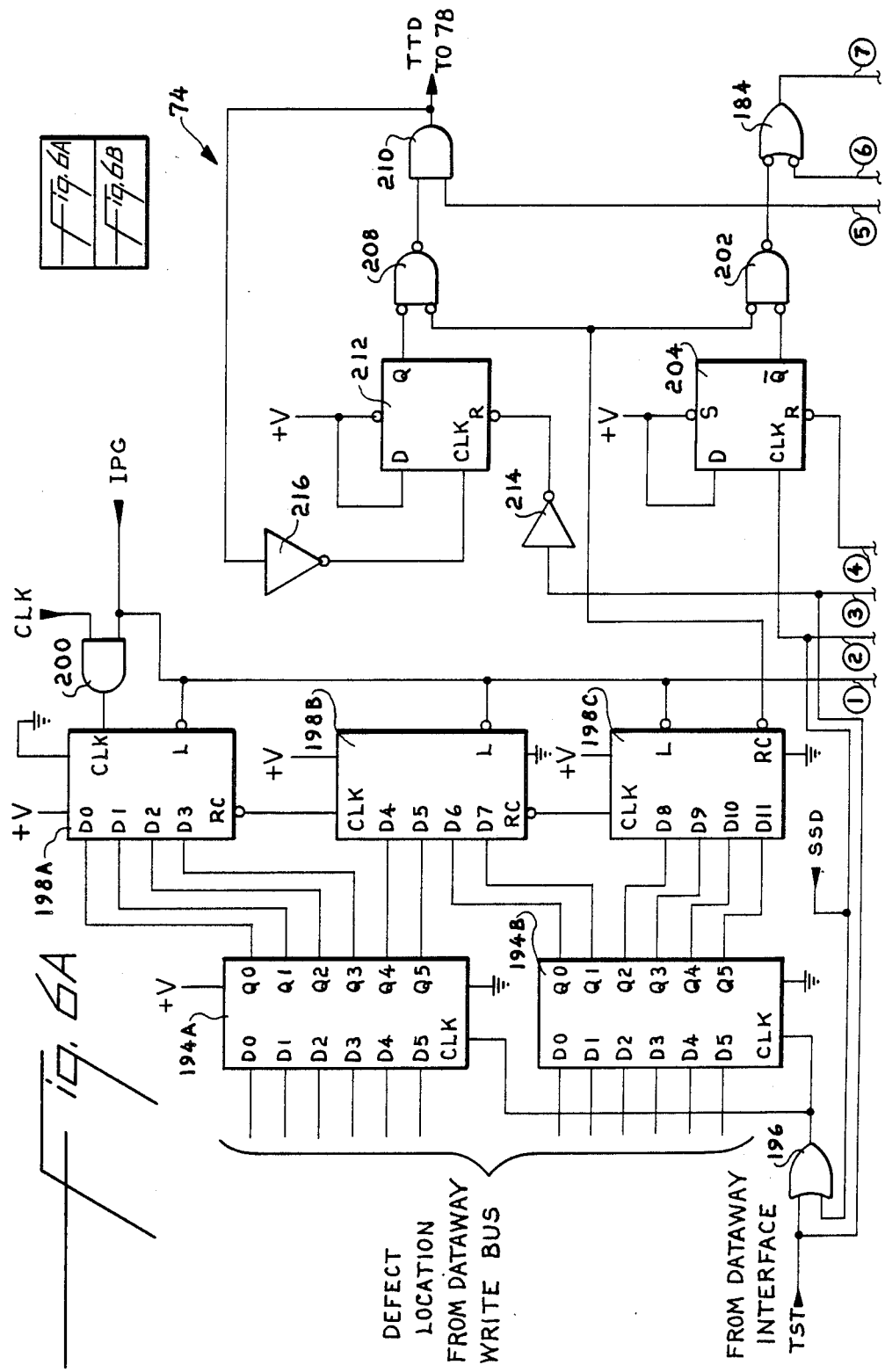

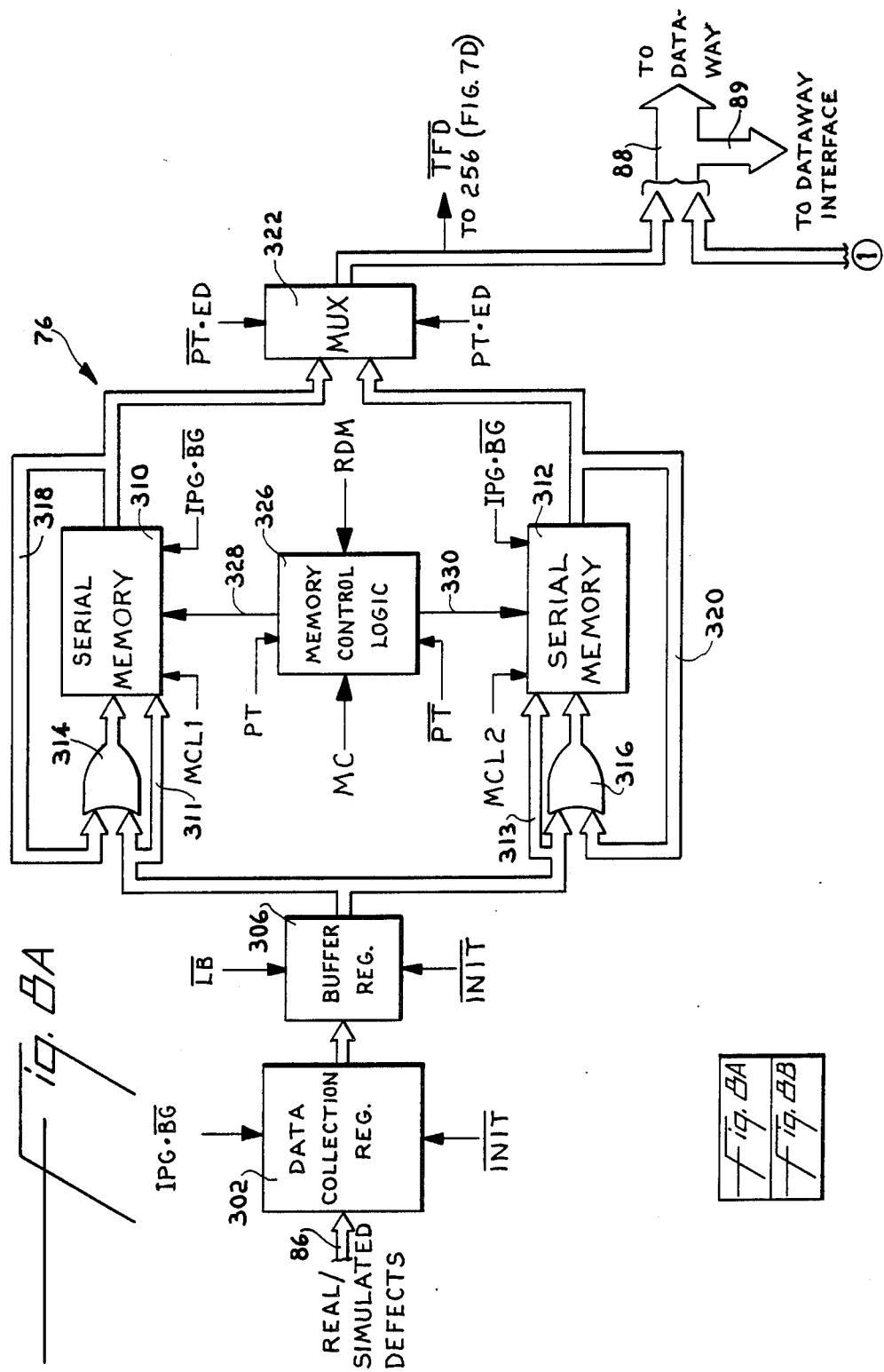

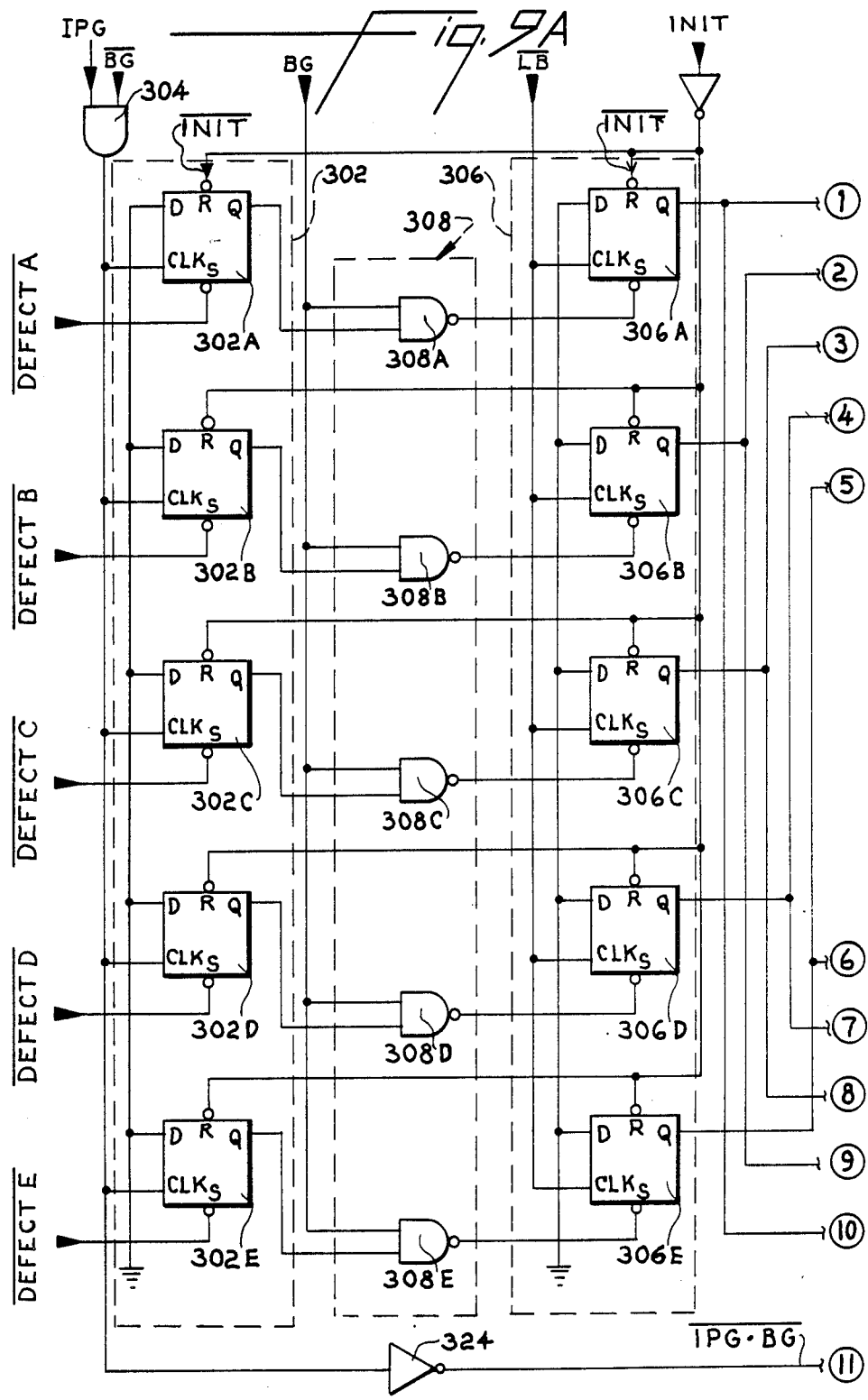

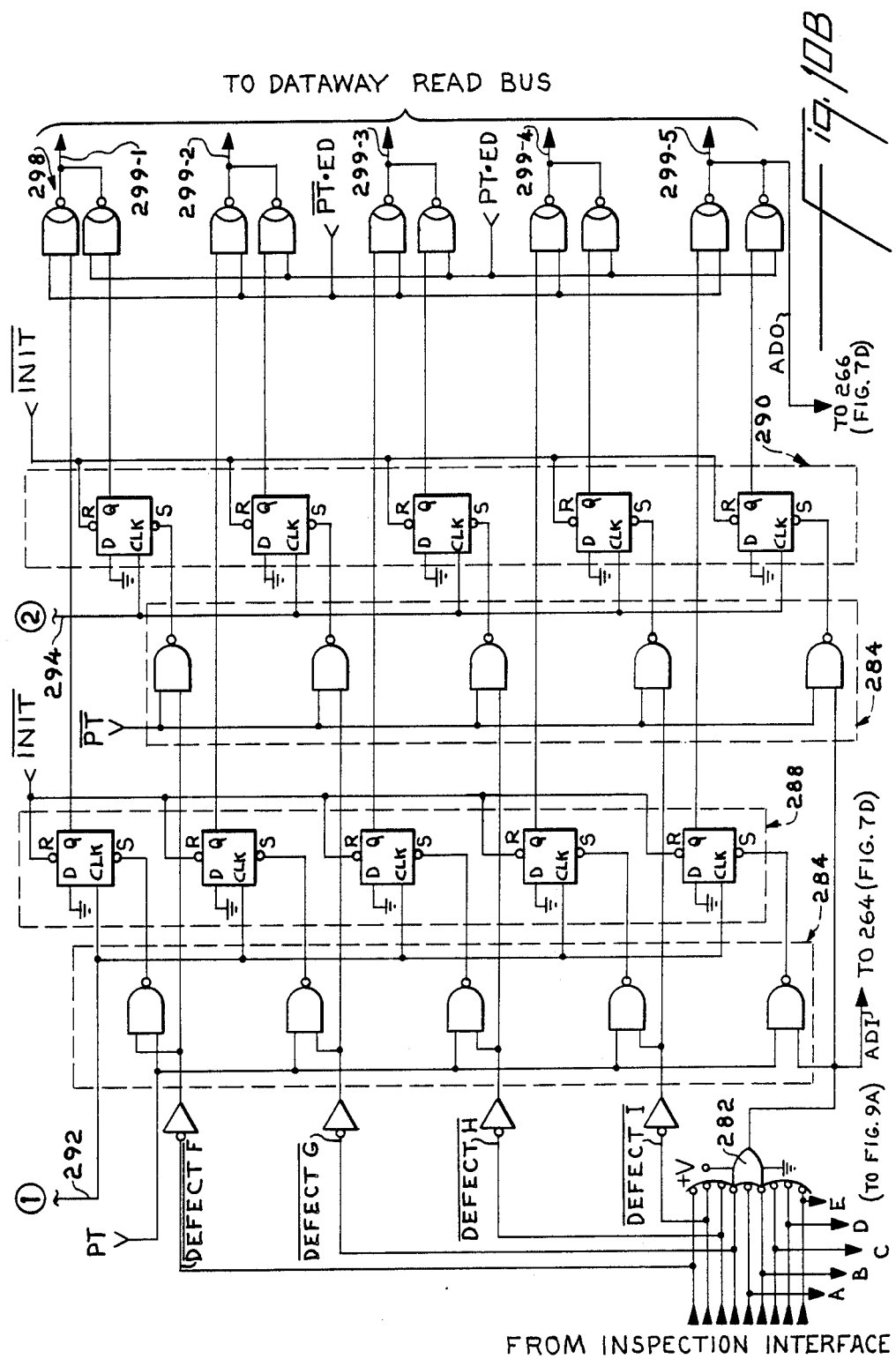

DATA COMPRESSION INTERFACE HAVING PARALLEL MEMORY ARCHITECTURE

FIELD OF THE INVENTION

This invention relates to an inspection system for inspecting web materials and, in particular, to an inspection system having a data compression interface with a streamlined memory architecture that utilizes serial memories connected in parallel.

DESCRIPTION OF PRIOR ART

Apparatus for inspecting continuous webs of sheet material for defects is well known. Typical of such apparatus is that described in U.S. Pat. Nos. 4,173,441 (Wolf), 4,134,684 (Jette) or 3,980,891 (Slaker). In such apparatus a rotating multifaceted mirror is used to direct radiation from a source, such as a laser, onto the web. The radiation is manifested as a "flying spot" which is caused to move along generally parallel scan paths which extend transversely of the web from edge-to-edge as the web is advanced beneath the mirror. Any predetermined number of scan paths may be used to electrically define a longitudinally extending portion of the web known as a "frame".

A detector, such as a photomultiplier tube, is positioned to receive radiation that is either transmitted through or reflected from the web. The detector is adapted to generate an electrical signal representative of the intensity of the radiation incident thereon. The magnitude of the electrical signal output from the detector contains information which may be used to indicate the presence of any one of a predetermined number of predetermined physical properties on that portion of the web through which the radiation incident on the detector passes or from which it reflects.

It is often advantageous to be able to determine whether certain physical properties are present in certain predetermined segments of each frame of the web. That is, it is often useful to ascertain whether certain physical properties are present in the right half segment, left half segment, etc., of each frame. To facilitate the generation of this information prior art inspection apparatus also includes an arrangement for electrically subdividing each scan path, and thus, indirectly, the web, into a predetermined plurality of transversely contiguous lanes. Thus, as the spot moves along each scan path it crosses each of the electrically defined lanes on the web. By locating a physical property with reference to a lane, it is easier to identify rapidly in which segment of a frame a property exists.

It may be readily appreciated that given the speed at which the spot traverses the web (typically one thousand scans per second), for a predetermined number of lanes (e.g., sixty-four) and for a predetermined number of physical properties (e.g., ten) there is produced during each frame a relatively large volume of digital data which must be transmitted from the inspection apparatus to the input ports of a local processor (typically a microcomputer) used to superintend the operation of the web inspection system. Transmission of such large volumes of data to the local processor requires a relatively high data rate (e.g., on the order of ten MHz.) with the attendant problems.

To compress the data generated during the inspection (and thereby reduce the volume of information that must be transmitted to the local processor within a given time interval) and to be able to more readily identify segments of the web in which certain physical properties are found, a system known as a lane data compression interface has been used.

This device, a block diagram of which is shown in FIG. 1, includes a random access read/write memory (Defect Memory) adapted to store real or simulated data representative of the actual or hypothetical occurrence of any of a predetermined number of physical properties, i.e., defects, in each of the lanes traversed as the spot of radiation moves along its scan path across the web. Predetermined storage locations in the Defect Memory are allocated to each lane and to each particular physical property of interest. These locations are addressed by an Address Generator. During a scan path across the web the address of the storage locations corresponding to each of the transversely contiguous lanes is applied to the Defect Memory. Thus, during the time corresponding to the movement of the spot over a given lane, real or simulated defect data detected in or hypothecated for that lane is latched into an Input Latch. The address from the Address Generator is incremented in response to a timing signal produced by an Input Timing Generator. Thus, as the spot physically moves along a given scan path across the web from one lane into the next adjacent lane the storage locations in the Defect Memory corresponding to those lanes are appropriately incremented.

The boundaries of the lanes are electrically defined by signals obtained from a Lane Boundary Memory. Any one of a predetermined number of families of lanes, each family containing a different configuration of lane sizes, may be selected by the Local Processor through appropriate lane family selection signals applied to a Lane Boundary Address Generator.

During each scan path in a frame (except for the first) the storage locations in the Defect Memory corresponding to each lane are updated with information concerning that lane derived during the current scan path. At the end of a frame the storage locations corresponding to each lane contain an accumulated summary which discloses whether any of the predetermined defects occurred anywhere in that lane during the frame. To avoid destruction of this information, another portion of the defect memory is used to store this information during the next or subsequent frames.

The accumulated defect information is output from the Defect Memory via an Output Latch to the Local Processor. Addressing of the Defect Memory for output purposes is also controlled by the Address Generator, this time in response to timing signals produced by an Output Timing Generator. However, since it is impossible to simultaneously write information generated during a current scan path into the Defect Memory and read information concerning a preceding frame from the Defect Memory, outputting the accumulated defect information can only be accomplished during those times when the spot is not interrogating the web. By requiring that information regarding a preceding frame may only be accessed and read from the Defect Memory during data nonacquisition times during a current frame leaves open the possibility that accumulated defect information may be lost.

To lessen the possibility of loss of information, a frame may be extended to include a greater number of scan paths. However this results in concomitantly lower resolution in locating defects on the web. If the operator desires that the web resolution remain unchanged, web speed must be lowered. However, this decreases throughput. Moreover, the "housekeeping" tasks of keeping track of what memory locations in the Defect Memory store what lane's information and remembering where in Defect Memory to resume a write operation once a read operation is finished (and vice versa) are complexities which, if eliminated, would free the local processor for other computational tasks.

Accordingly, in view of the foregoing, it is believed to be advantageous to provide a data compression interface which utilizes a more efficient and streamlined memory architecture thereby avoiding the complexities which are a perceived disadvantage with the prior system. It is also believed advantageous to provide a memory architecture which more quickly and efficiently permits transfer of accumulated defect information regarding a preceding frame, thus permitting the data compression interface to have a higher resolution at a given operating speed than is available with the prior system. In addition, it is also believed advantageous to provide a data compression system with a circuit arrangement which would permit the inspection system's operating status to be self-checked and remotely monitored, e.g., by the local processor, in order to improve operating reliability.

SUMMARY OF THE INVENTION

In accordance with the present invention provided is a web inspection system having a data compression interface with a streamlined memory architecture which avoids the disadvantages perceived in the prior art system. The web inspection system comprises flying spot generator in the form of a source of interrogating radiation and means for moving a spot of radiation transversely of the web along a plurality of generally parallel scan paths. The web is subdivisible into a plurality of frames, each of which is comprised of a predetermined plurality of transverse scan paths. Each scan path is further subdivisible into a predetermined plurality of transversely contiguous lanes.

A detector, such as a photomultiplier tube, is responsive to the interrogating radiation transmitted through or reflected by the web and is adapted to generate an electrical pedestal signal representative thereof.

A discriminator is responsive to the pedestal signal for generating an electrical characteristic signal representative of the presence of a predetermined physical property of the web at a corresponding lane of the scan path along which the spot moves.

The output of the discriminator is connected to the data compression interface. The interface includes first and second serial memories connected in parallel. Each memory has a number of stages that corresponds to the number of lanes defined along a scan path. A memory selector network is provided for selecting, during each frame, one of the memories as an input memory and the other of the memories as an output memory. Thus, a memory serves as the input memory during alternate frames.

During each scan path in a frame the input memory is sequentially shifted in synchronism with the movement of the spot across the lanes of the web. At the end of any given scan path, the stage in memory corresponding to the first lane of that scan path occupies the final position in the memory, while the stage in memory corresponding to the last lane of that scan path occupies the initial position in the memory.

In the course of the first scan path in a frame, if the discriminator produces an indication of the presence of a predetermined physical property in a given lane, a characteristic signal representative of this fact is directly loaded into the stage of the input memory corresponding to that lane. Throughout each subsequent scan path of that frame the contents of each stage of the input memory recirculate and are logically summed with signals representative of the physical property detected during the current scan path to thus produce, at the end of that scan path, an accumulated summary of the lane-by-lane occurrence of a predetermined physical property in that portion of the frame theretofore interrogated.

The particular serial memory selected as the output memory contains an accumulated lane-by-lane summary of the occurrence of the predetermined physical property generated during the preceding frame of the web. During a current frame, the output memory may be read independently of and asynchronously with respect to the generation of the lane-by-lane summary of the current frame.

First and second storage latches connected in parallel are selectable during alternate frames as an input latch. The input latch stores a second characteristic signal output from the discriminator representative of a second predetermined physical property of the web. The storage of the second characteristic signal provides an indication of the occurrence of the second property without regard to the lane in which the second property occurred. The other latch is selectable as an output latch from which the indication produced during the preceding frame is read.

Throughout its operation status signals are generated representative of the application, during a given frame, of a characteristic signal to the input memory or input latch and of the transmission, during a subsequent frame, of a signal out of that memory or latch. These status signals are applied to an array of registers which may be periodically monitored by the local processor to ascertain the operating status and operability of that memory or latch. The interrogation of the status registers is independent of the generation or reading of the accumulated lane-by-lane summaries.

BRIEF DESCRIPTION OF THE DRAWINGS

The present invention will be more fully understood from the following detailed description thereof taken in connection with accompanying drawings which form a part of this application and in which:

FIG. 1 is a block diagram of a prior art data compression interface for a web inspection system;

FIG. 2 is a stylized pictorial representation of a web inspection apparatus with which the data compression interface in accordance with the present invention is used;

FIG. 3 is a block diagram of the data compression interface of the present invention;

FIGS. 4A and 4B are detailed schematic diagrams of the timing generator module used in the data compression interface in accordance with the present invention;

FIGS. 6A and 6B are detailed schematic diagrams of the Inspection Bus interface module used in the data compression interface in accordance with the present invention;

FIGS. 8A and 8B are functional block diagrams of the memory module of the data compression interface in accordance with the present invention;

FIGS. 9A, 9B and 9C are detailed schematic diagrams of the portion of the memory module used to produce and store a lane-by-lane summary of lane-oriented defects;

FIGS. 10A and 10B are detailed schematic diagrams of the portion of the memory module used to produce and store a summary of nonlane-oriented defects;

DETAILED DESCRIPTION OF THE INVENTION

Figure 4B:
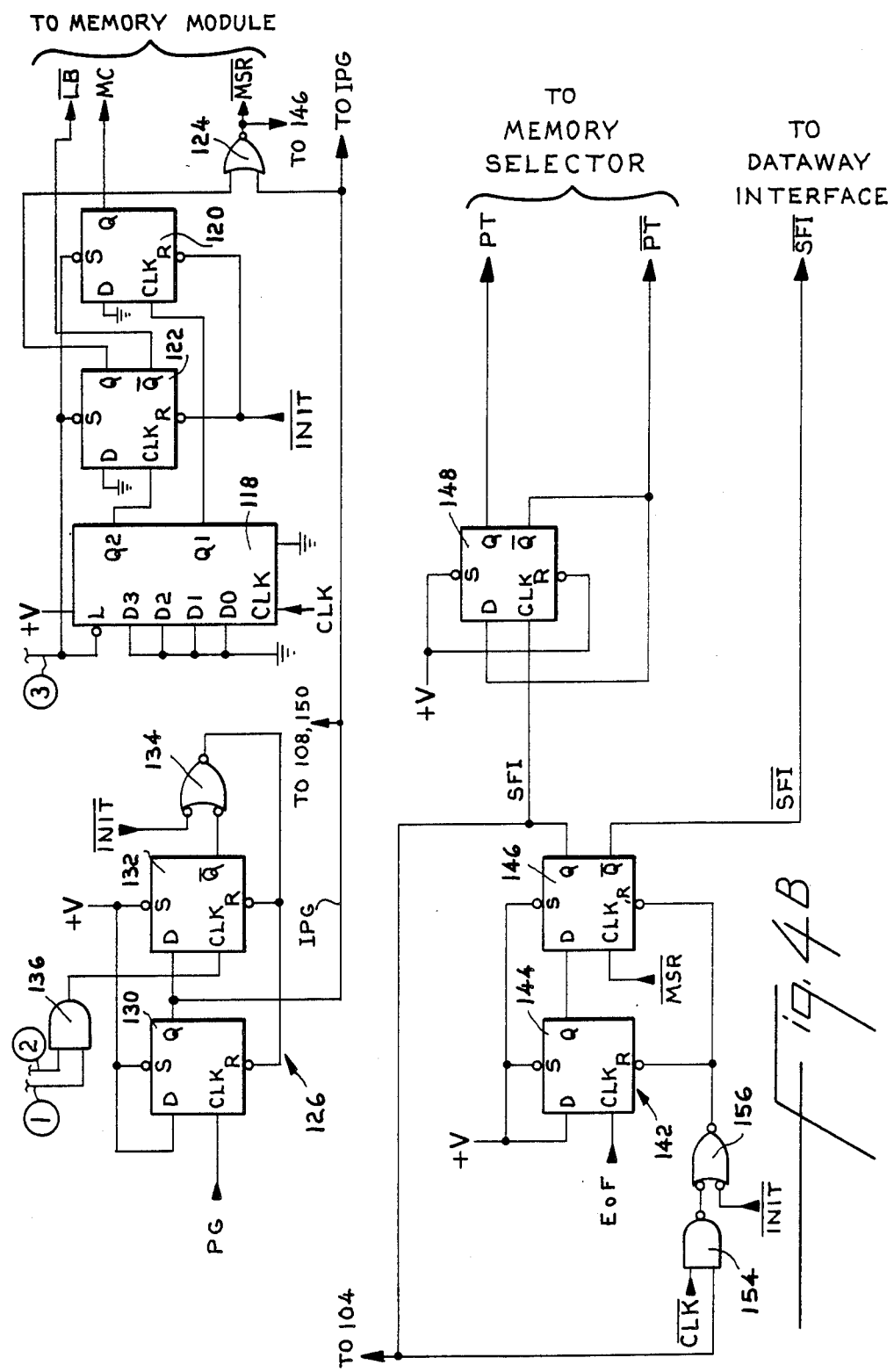

Throughout the following detailed description similar reference numerals refer to similar elements in all figures of the drawings.

Shown in FIG. 2 is a stylized pictorial representation of a web inspection apparatus with which the data compression interface 20 in accordance with the present invention may be used. The web inspection system includes a flying spot generator which includes a source 22 of interrogating radiation such as a laser. The source 22 cooperates with a multifaceted rotatable mirror 24 to generate a spot 26 of interrogating radiation. Rotation of the mirror 24 in the direction of the arrow 28 causes the spot 26 to be moved over the web W along each of a plurality of generally parallel scan paths 30. Each scan path 30 extends transversely across the width of the web W from the lateral leading edge L to the lateral trailing edge T as the web W is moved longitudinally past an inspection point 32 in the direction of the arrow 34. The edges L and T demarcate that part of the web W which is coated, treated, or otherwise defines product to be inspected. The web W may be provided with margins (not shown) disposed laterally outwardly of the product part of the web W defined by the edges L and T. A shaft encoder 36 associated with the web drive generates electrical signals on a line 38 representative of the longitudinal velocity of the web W.

The web W is subdivisible into a plurality of frames 40. Each frame is an arbitrary increment of web W measured in the direction 34 of web travel. Each frame includes a predetermined number of scan paths 30. As is discussed hereafter each scan path 30 is electrically subdivisible into a plurality of lanes 42. The lanes 42 may be envisioned as transversely contiguous, longitudinally extending portions of the web W. Any convenient number of lanes 42 may be electrically defined along each scan path 30. In addition, as discussed herein, the width dimension of each lane is determined by the selection of any one of a predetermined number of lane size families. Each lane size family contains a different combination of individual lane sizes. In the embodiment of the invention discussed herein, sixty-four lanes are defined along each scan path. Each lane size, measured in terms of system clock counts, must be such that the sum of all lane sizes is less than the time between the beginning of successive scan paths across the web W.

A detector 44, such as a photomultiplier tube, is disposed at the inspection point 32 in a convenient location with respect to the web W. The detector 44 may be located beneath the web (as shown in FIG. 2) in order to respond to radiation transmitted through the web W as the flying spot 26 of interrogating radiation traverses each scan path 30. Of course, equally within the contemplation of this invention is an inspection apparatus in which the detector 44 is positioned with respect to the web W so as to respond to radiation reflected from the web W.

Radiation incident upon the detector 44 results in the generation of an analog electrical voltage pedestal signal the profile of which is shown in FIG. 2. The magnitude of the pedestal signal at any point thereof is functionally related to the physical properties of the web W at the corresponding physical position of the spot 26 along the scan path 30. The output of the detector 44 is suitably amplified and applied to a signal processing discriminator network 45. In the discriminator various signal processing techniques, e.g., differentiation, are applied to the raw pedestal signal to make easier the discrimination of certain predetermined physical properties of the web W. The processed signal is compared to a threshold set by a potentiometer 47 in a comparator 46. The signal output from the comparator 46, called Product Gate (PG), is carried by a line 48 as part of the Inspection Bus 49 to the data compression interface 20.

The processed signal is also applied to an array of defect discriminators configured from comparators 50A–50I. Each of the comparators 50 receives an appropriate threshold level from an associated potentiometer 52.

An output on an associated line 54 from any one of the comparators 50 is an electrical characteristic signal representative of the fact that the web W, at the corresponding physical position of the spot 26, exhibits a predetermined physical property which is classifiable as a defect. Typical examples of defect types are catalogued in U.S. Pat. No. 3,843,890 (Anthony et al), assigned to the assignees of the present invention. Throughout the remainder of this application the presence of characteristic signals on the lines 54 from the respective comparators 50 shall be representative of the occurrence of certain predetermined physical properties hereafter referred to as signals representative of defects A through I, respectively. The output lines 54 constitute a part of the Inspection Bus 49. (On FIG. 3, the lines 54 from the comparators 50 are collectively referred to as discriminator outputs or "Disc. Outputs".) Any predetermined number of physical properties may be accommodated by appropriate modification to the interface 20 and remain within the contemplation of the present invention.

Some of the defects, e.g., the defects A through E producing signals from the comparators 50A through 50E, are categorized as "lane-oriented" defects. It is advantageous with defects of this class that an inspector be made aware of not only the existence of such a defect anywhere in a frame 40, but also the transverse position, i.e., lane 42, at which such a defect occurred. This information is useful in determining, e.g., where a web should be sheared in order to salvage usable material. Defects F through I, which respectively produce outputs on the lines 54F through 54I from the comparators 50F through 50I, are known as "nonlane-oriented" defects. For defects of this class it is advantageous that an inspector be aware that such defects have occurred within a frame, since these defects are typically of such a nature that their presence anywhere in a frame could render the entire frame unusable. Both lane-oriented and nonlane-oriented defects should be included in any accumulated summary of defects within a given frame.

The output line 38 from the shaft encoder 36 is applied to a divide-by-N counter 56. The output line 58 from the counter 56 carries the signal Selected Scan (Sel. Scan) which is asserted during only preselected ones of the scan paths 30. Because the speed of the web W in the direction 34, the speed of the spot 26 across the web W and the physical dimensions of the spot 26 are such that the spot 26 repeatedly scans over the same swath of the web W before the web W is advanced sufficiently relative to the inspection point 32 beneath the mirror 24, the signal Sel. Scan on the line 58 is used to enable the data compression interface 20 only during that one scan path out of N number of scan paths 30 in which the spot 26 is interrogating a swath of web W that has not been theretofore interrogated.

The output from the counter 56 is also applied to an up-counter 60. The output from the counter 60 on its associated line 62 represents an End of Frame signal (EoF) which, as its name implies, is asserted when a predetermined number of Sel. Scan signals have occurred. The End of Frame signal indicates the end of a given frame 40 and the start of a succeeding frame on the web W. Both the signal Sel. Scan on the line 58 and the signal EoF on the line 62 are applied to the data compression interface 20 over the Inspection Bus 49.

A clock signal (CLK) on a line 64 is derived from a five MHz. crystal oscillator 66 which serves as the system clock. The signal CLK is also applied to the data compression interface 20 by the Inspection Bus 49 and is used to derive timing pulses used in the logic circuitry thereof.

The data compression interface 20 communicates with a local processor 68 over a bidirectional Dataway 70. The Dataway 70 complies with the IEEE CAMAC Standard 583 (1975). Thus, the Dataway 70 includes the data-read bus, data-write bus, address bus, and function and timing lines extending between the local processor 68 and its peripheral, the data compression interface 20, as mandated by the CAMAC Standard. Suitable for use as the local processor 68 is a minicomputer such as that manufactured by Digital Equipment Corp. under model number DEC 11/23.

The local processor 68 itself communicates with a host processor 72 (similar to the processor 68) which superintends the operation of the local processor 68 and those other local processors included as part of the overall distributed processing system which exercises control of the plant of which the web inspection apparatus is but a part.

OVERVIEW OF DATA COMPRESSION INTERFACE

Referring to FIG. 3 shown is a block diagram of the data compression interface 20 in accordance with the present invention. The CAMAC-compatible lane defect data compression interface 20 is a high speed digital system which, from the point of view of the local processor 68, is adapted to monitor the asynchronously occurring outputs of the comparators 50 in real time and to formulate a group of multibit digital words for each frame. Each multibit word corresponds to a particular type defect (either lane-oriented or nonlane-oriented). Each multibit word is, for a lane-oriented defect, an accumulated end of frame summary of the lane-by-lane occurrence in a frame 40 of that defect (property). The digital words are transmitted in parallel (lane bit by lane bit) via a memory output bus 88 to the Dataway 70 that connects the data compression interface 20 to the local processor 68. Provision is made whereby simulated defects of each predetermined defect type can be located within any predetermined lane to verify the operation of the inspection system. Simulated defects may be entered by the operator via external switches or by the host processor. The interface 20 also includes a status register arrangement which may be used to permit the local processor 68 to monitor operation of the data compression interface 20.

As seen from FIG. 3, the data compression interface 20 comprises four main modules, or subsystems. These modules are the Inspection Bus interface module 74, the memory module 76, the Dataway interface module 78 and the timing generator module 80.

The Inspection Bus interface module 74 is adapted to receive actual and simulated discriminator characteristic signals and provide them to the memory module 76. Actual defect characteristic signals from the comparators 50 are received from the Disc. Outputs lines 54 of the Inspection Bus 49. Simulated defects imposed upon the inspection system by the local processor 68 are received via the write bus of the Dataway 70. Simulated defects can be imposed locally by the operator through an array of three binary coded decimal thumbwheel switches 82. Simulated defect-type is selectable by the setting of one of the thumbwheel switches 82 ("Type"). Simulated defect location, in terms of the lane in which the defect is to reside, is selected by the settings of the other two of the thumbwheel switches 82 ("Loc."). An enter defect pushbutton 84 is used to effect the entry of the operator-selected simulated defects into the Inspection Bus interface module 74. A binary digit representing the occurrence of each of the defect types A through I (whether of real or simulated origin) is applied over a memory input bus 86 to the memory module 76.

In the memory module 76, the multibit words representing the accumulated lane-by-lane summary of lane-oriented defects and the summary of nonlane-oriented defects in a frame are produced. The lane-oriented and nonlane-oriented defects are applied to the memory module 76 on their respective lines of the memory input bus 86 and are appropriately segregated and stored. Any nonlane-oriented defect (i.e., defect type F through I) occurring or imposed on the system during a scan path is latched in the appropriate one of a plurality of storage latches in one of a plurality of storage latch arrays. Each storage latch array includes a storage latch for each nonlane-oriented defect type and a latch for an "Any Defect" signal. At least two such latch arrays are required. One array of latches is selected as an input, or data collection, latch array during each frame. The other of the latch arrays serves, during that same frame, as an output latch array which is read onto the read bus of the Dataway 70 over a memory output bus 88.

Lane-oriented defect occurrences (i.e., defect types A through E) are double buffered and stored in one of a plurality of serial memories synchronously with the movement of the spot across each scan path in the frame. At least two serial memories are required. The serial memories are connected in parallel. One serial memory is selected by a memory selector network during alternate frames as an input or data collection memory. The other serial memory serves, during the same frames, as an output memory. The output memory is read onto the memory output bus 88 to the Dataway 70 asynchronously with respect to the collection of data by the input memory. Signals on the memory output bus are also applied over a bus 89 to the status register arrangement in the Dataway interface module 78.

Each serial memory is comprised of an array of serial memory elements. Each memory element has a predetermined number of banks therein. Thus, each serial memory includes a number of memory banks corresponding to the number of lane-oriented defect types being stored. An additional bank is provided for a Transfer Done Flag bit. Each memory bank has the same number of stages as there are lanes in the scan path. Any predetermined number of stages (i.e., lanes) may be used and remain within the contemplation of the present invention.

During the first scan path in any frame, lane-oriented defect data is directly loaded into the input memory. Data is serially entered and shifted into a bank until, at the end of the first scan path, information regarding the first lane resides in the last memory stage while information relating to the last lane occupies the first stage. During each subsequent scan path information regarding the presence of a particular type of defect in each lane of the current scan path is logically summed in a logic network (connected intermediate the discriminator 45 and the serial memory input) with information regarding defects previously stored for that lane during earlier scan path so that each bank provides an accumulated lane-by-lane summary of the occurrences of lane-oriented defects during a frame. The logic network is bypassed only during the first scan path in each frame.

The Dataway interface module 78 is connected to the read bus, write bus, address bus, function and timing lines of the Dataway 70. Signals applied from the local processor 68, or from the host processor 72 via the local processor, are appropriately routed from the Dataway interface 78 to the various modules which comprise the data compression interface 20. In addition, the Dataway interface module 78 includes a status register arrangement which holds status signals representative of the occurrence of various of the data compression interface's activities whereby such activities can be monitored by the local processor 68 via an output bus 90 connected to the Dataway read bus. In particular, the register arrangement stores a first status signal (the Any Defect In signal ADI) representative of the application of a characteristic signal to the memory (or latch) selected during the frame as the input memory (or latch) and a second status signal (the Any Defect Out signal ADO) representative of the transmission of a signal out of that memory or latch during the next subsequent frame to provide a monitorable (by the local processor) indication of the operability of the input memory (or latch).

The timing generator module 80 serves to provide necessary timing signals used in the operation of the modules 74, 76 and 78 which comprise the data compression interface 20.

TIMING GENERATOR MODULE

Shown in FIGS. 4A and 4B is a detailed schematic diagram of the timing generator module 80 of the data compression interface 20. The timing generator module 80 generates timing signals needed in the operation of the data compression interface 20.

A latch 102 has its data inputs connected to three of the write lines on the Dataway write bus. These lines carry the three bit code from the host processor (via the local processor 68) which identifies the lane size family selected by the host processor 72. Dependent upon the lane size family selected the lanes may exhibit various predetermined width dimensions.

The latch 102 is clocked by the Select Lane Family signal (SLF) produced by the Dataway interface module 78. The outputs of the latch 102 are connected to a second latch 104 which is clocked by the Synchronized Frame Increment signal (SFI) produced in the timing generator 80 in the manner to be discussed herein. Suitable for use as each of the latches 102 and 104 are devices made by any semiconductor manufacturer, e.g., Texas Instruments and sold under model number 74LS175.

The output of the latch 104 is applied to the three most significant address ports of a lane size memory 106. Suitable for use as the lane size memory 106 is a programmable read-only memory such as that sold by Intel under model number 3628. The outputs of the latch 104, representing the three most significant bits of ROM address, are also applied over lines RA8, RA7 and RA6 to the status register arrangement in the Dataway interface module 78. The remaining six address lines to the lane size memory 106 are derived from the outputs of up-counters 108A and 108B. Suitable for use for the counters 108 are those manufactured by, e.g., Texas Instruments under model number 74LS191.

The outputs of the lane size memory 106 are applied to down-counters 110A and 110B (similar to the counters 108). The outputs of the counters 110 are inverted (except for the Q1 output) and applied to a multiple input NAND gate 112 the output of which defines the complement of the Simulated Defect Count signal (DSC-NOT) applied to the Inspection Bus interface 74. The output of the gate 112 is connected to the set input of a buffer gate flip-flop 114. The outputs of the flip-flop 114 are the Buffer Gate signals (BG and BG-NOT) used in the memory module 76.

The ripple carry (RC) output of the down-counter 110A is connected as one input of a gate 116. The output of the gate 116 resets the buffer gate flip-flop 114, loads the down-counters 110A and 110B and clocks the up-counters 108A and 108B. In addition, the ripple carry (RC) output of the down-counter 110A is applied to load an up-counter 118 (FIG. 4B). The Q1 output of the counter 118 clocks a memory clock flip-flop 120. The Q output of the flip-flop 120 is the Memory Clock signal (MC) used in the memory module 76. The Q2 output of the counter 118 clocks a lane boundary flip-flop 122. The Q-NOT output of the flip-flop 122 defines the complement of the Lane Boundary signal (LB-NOT). The Q output of the lane boundary flip-flop 122 is NOR-ed by a gate 124 with the signal Internal Product Gate (IPG) to produce the complement of a signal Memory Select Reset (MSR-NOT) used in the memory module 76.

The Internal Product Gate signal IPG is produced by a signal generator logic generally indicated by reference character 126. The logic 126 includes a first flip-flop 130 which receives the Product Gate signal PG from the Inspection Bus 49 at its clock input. The Q output of the flip-flop 130 defines the Internal Product Gate signal IPG. The Q output of the flip-flop 130 is also applied to the data input of a second flip-flop 132. The Q-NOT output of the flip-flop 132 is fed back through a gate 134 to reset both of the flip-flops 130 and 132. Flip flop 132 is clocked through an AND gate 136 which derives its inputs from predetermined ones of the outputs of the up-counters 108A and 108B (FIG. 4A).

The Synchronized Frame Increment signal SFI is derived from a signal generator generally indicated at reference character 142. This network includes a first flip-flop 144, the Q output of which is applied as the data input to a second flip-flop 146. The Q output of the flip-flop 146 defines the Synchronized Frame Increment signal SFI. The signal SFI clocks the latch 104 (FIG. 4A). Its complement, SFI-NOT, is applied to the Dataway Interface module 78. The SFI signal is also applied to clock a pointer flip-flop 148. The Q output of the flip-flop 148 defines the Pointer signal (PT) while the complementary signal (PT-NOT) is derived from the Q-NOT output. These signals are used in the memory module 76. Suitable for use as the flip-flops 114, 120, 122, 130, 132, 144, 146 and 148 are devices sold by, e.g., Texas Instruments under model number 74LS74.

Figure 5A:
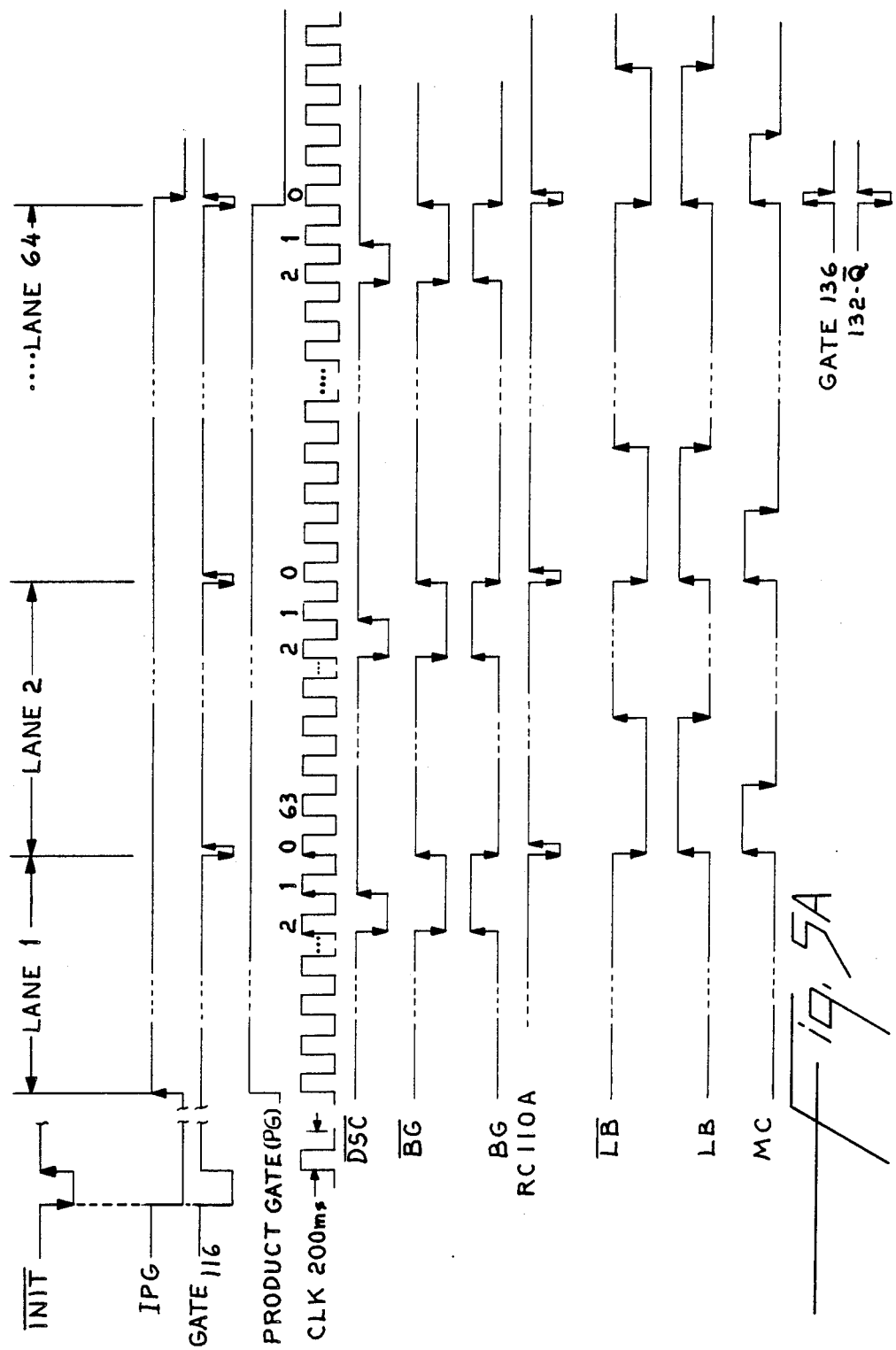
FIGS. 5A and 5B are timing diagrams of timing signals generated during the operation of the timing generator module shown in FIGS. 4A and 4B.
Figure 5B:
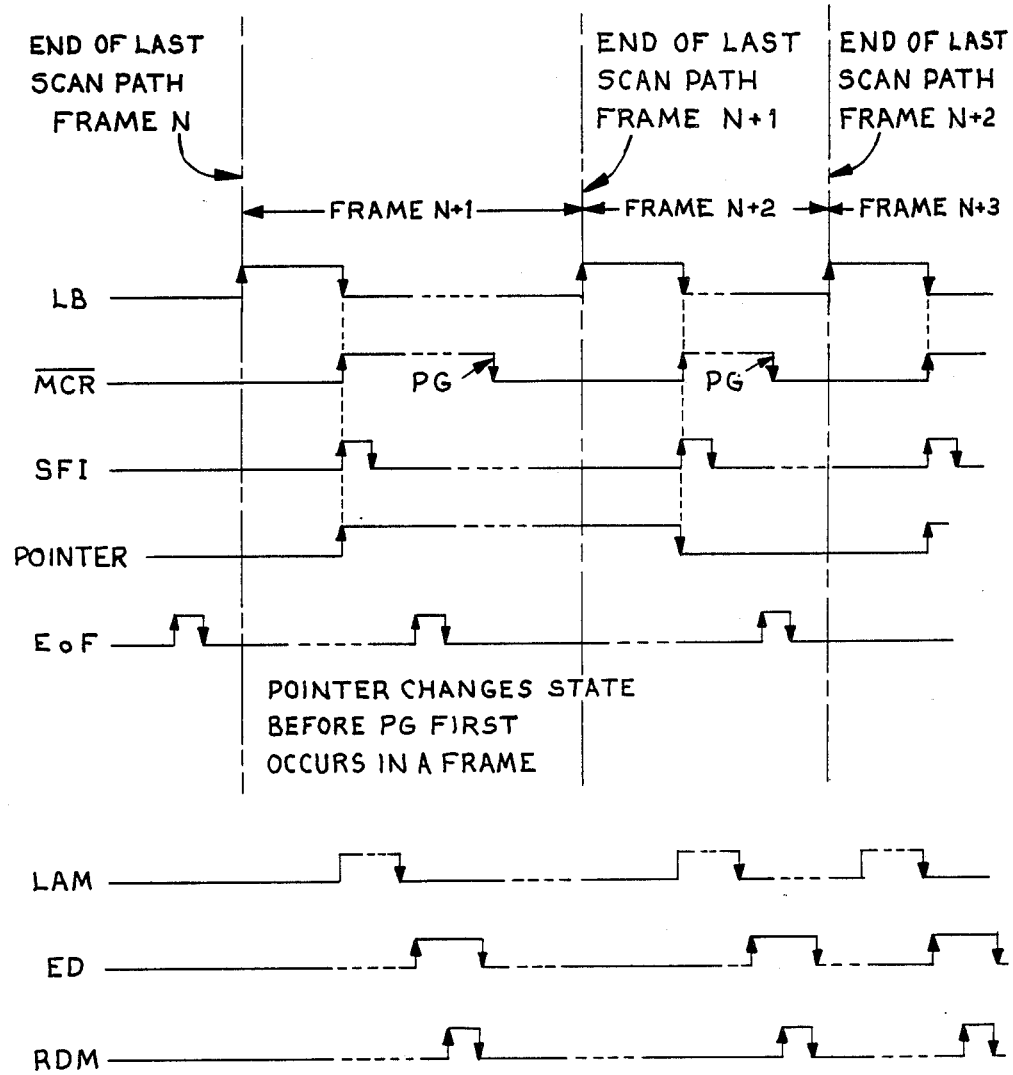

The operation of the timing generator module 76 may be better understood in conjunction with timing diagram FIGS. 5A and 5B. As seen in FIG. 5A, upon power up the signal INIT-NOT derived from the Dataway Interface module 78 is applied through the gate 134 and resets the flip-flops 130 and 132. This causes the load lines of the address counters 108A and 108B to go low. The least significant data bit input (D0) of the counter 108B is also taken low by the signal INIT-NOT. This causes the output of the counters 108A and 108B to be zero. The output of these counters form part of the address for the lane boundary memory 106. The three most significant bits of the memory address are derived from the latch 104. The memory 106 stores eight families of numbers defining in binary notation the width of each of the lanes 42 in system clock counts. (In the preferred embodiment discussed in detail herein, there are sixty-four lanes defined along each scan path 30 although, as noted, any predetermined number of lanes may be used.). The local processor 68 can select any of the eight lane families by loading a three bit number into the latch 102. However, at initialize time, contents of both the latches 102 and 104 are zero due to the clearing action of the INIT-NOT signal. The output of the memory 106 will then be a binary number (stored at memory address zero) representing the width in system clock counts of the first lane.

This binary number is loaded into the down-counters 110A and 110B by a low level on their load inputs caused by the action of the signal INIT-NOT through the gate 116. At the end of the initialize period the load terminals of the down-counters 110A and 110B will go high and the counters 110 will contain the size (in system clock counts) of the first lane. The low order data bit (D0) of the up-counter 108B will go high at the end of the initialize period. However, the load lines of the counters 108 will remain low since the signal IPG is low. The up-counters 108 are thus incremented, which causes the output of the memory 106 to represent the size in binary clock counts for the second lane. This information, although present at the inputs to the counters 110, is not loaded thereinto.

As seen from the timing diagram FIG. 5A the leading edge of the Product Gate signal PG on the Inspection Bus 49 clocks the flip-flop 130 causing the Internal Product Gate signal IPG derived from the Q output thereof to go high. This releases the load lines on the counters 108. The signal IPG going high opens the AND gate 150 and allows the signal CLK carried by the Inspection Bus 49 to begin downcounting the first lane size stored in the down-counters 110. When the downcount equals two (i.e., the Q1 output of the counter 110B is high) the output of the gate 112 will transition low for a predetermined time, generating the DSC-NOT signal and setting the flip-flop 114 to generate the buffer gate signal BG and its complement BG-NOT. The next down count terminates the signal DSC-NOT. A predetermined time later (four hundred nanoseconds) the counter 110B will go to zero, producing a logic low on the ripple carry output (RC) of the counter 110A. This will produce a logic zero at the output of the gate 116 which will reloads the counters 110 with the count for the next (second) lane already present on its data input terminals. The low-going output of the gate 116 will also reset the flip-flop 114 causing the Buffer Gate signals to transition. The ripple carry output (RC) of the counter 110A will also set flip-flops 120 and 122, which respectively generate the Memory Clock signal MC and the complement of the Lane Boundary signal LB-NOT. The complement of the signal Memory Select Reset MSR-NOT is also generated. Ripple carry (RC) from the counter 110A going to zero will also load a zero into the up-counter 118 and will increment the counters 108A and 108B (through the gate 116) causing the next (third) lane size to appear at the data inputs of the counters 110. (This terminates the ripple carry output and the low output of the gate 116.) Four hundred nanoseconds later, the Q1 output of the counter 118 will transition, clocking flip-flop 120 to terminate the Memory Count signal MC. After another four hundred nanoseconds, the Q2 output of the counter 118 will go high, clocking the flip-flop 122 and terminating both the complementary lane boundary signal LB-NOT and the Memory Select Reset signal MSR-NOT.

This process is repeated at the end of each lane until the trailing edge of the sixty-fourth lane. At that time, counters 108 will be clocked and the output will go to a count of sixty-four (the last lane). This will produce a high level at the output of the gate 136 which will clock the flip-flop 132. This in turn resets both flip-flops 130 and 132 through the action of the gate 134 and causing the Internal Product Gate signal IPG to go low. The Internal Product Gate signal IPG will remain low until the next leading edge of the Product Gate signal PG again clocks the flip-flop 130 repeating the process. During the sixty-fourth lane, the address on the memory 106 is zero. Therefore, the down counters 110 will be reloaded with the count for the first lane of the next scan path and will hold that count until the start of the next scan path.

AND gates 152, connected to the address inputs of the memory 106, are used to decode the binary count representing lane sixty-three. When the memory address reaches a count of sixty-four, the sixty-third lane is being generated. The output of the gates 152 and the high order output of the counter 108A will be high during lanes sixty-three and sixty-four respectively. These two signals, along with the three significant address bits specifying the lane family are applied to the status register arrangement in the Dataway interface module 78. During the period from the end of one scan path to the beginning of the next scan path the counters 108 will be loaded with the count of one in preparation for the end of the first lane on the next scan path.

The Synchronized Frame Increment signal SFI is generated through the network 142. As seen from FIG. 5B, the End of Frame signal EoF is asynchronously received on the Inspection Bus 49 and clocks the flip-flop 144 to set the Q output high. At the trailing edge of the last Lane Boundary signal LB on the scan path, the output of the gate 124 (MSR-NOT) will go high. If an End of Frame signal EoF has occurred, the data input to the flip-flop 146 will be high and will be clocked by the rising edge of the signal MSR-NOT thus setting the Q output high. The Synchronized Frame Increment signal SFI thus generated clocks the pointer flip-flop 148, complementing the Pointer signal outputs. The Synchronized Frame Increment signal SFI is also applied to one input of a NAND gate 154, the other input of which is derived from the inverted system clock CLK. The SFI signal will cause the output of the gate 154 to go high. Since this will occur on the leading edge of the system clock, the inverted CLK signal on the other input pin of the gate 154 will be low. The output of gate 154 will remain high for one hundred nanoseconds, or half a clock period, until the system clock CLK falls causing both the flip-flops 144 and 146 to be reset through the gate 156, thus clearing the Synchronized Frame Increment signal SFI. This operation will produce a one hundred nanosecond SFI signal at the end of the last Lane Boundary signal LB in a scan path if an End of Frame signal EoF had occurred previously.

Figure 7A:
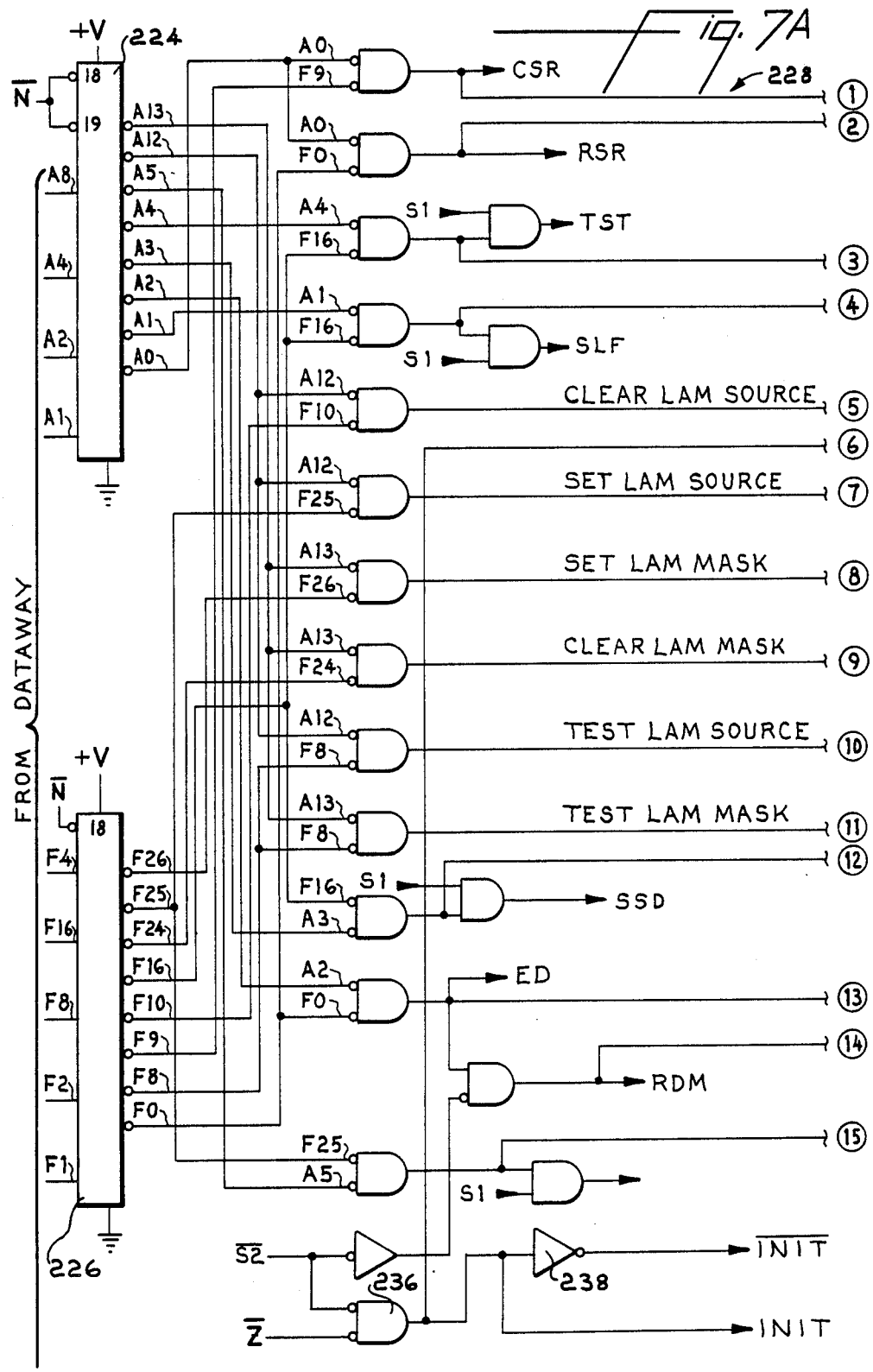
FIGS. 7A, 7B, 7C, and 7D are detailed schematic diagrams of the Dataway interface module used in the data compression interface in accordance with the present invention.

As previously alluded to, the local processor can select any one of eight lane boundary patterns by writing a three bit code onto the Dataway Write Bus and driving predetermined address line (A1) and function line (F16) (See FIG. 7A). The Dataway interface module 78 decodes the address and function and combines them with the timing signal S1 to produce the Select Lane Family signal SLF. This signal strobes the lane family code into the latch 102. Contents of this latch will be transferred to the latch 104 at the end of the data collection frame by the SFI pulse. These three most significant bits of the memory address select the corresponding family of sixty-four lane sizes.

INSPECTION BUS INTERFACE MODULE

Figure 6B:
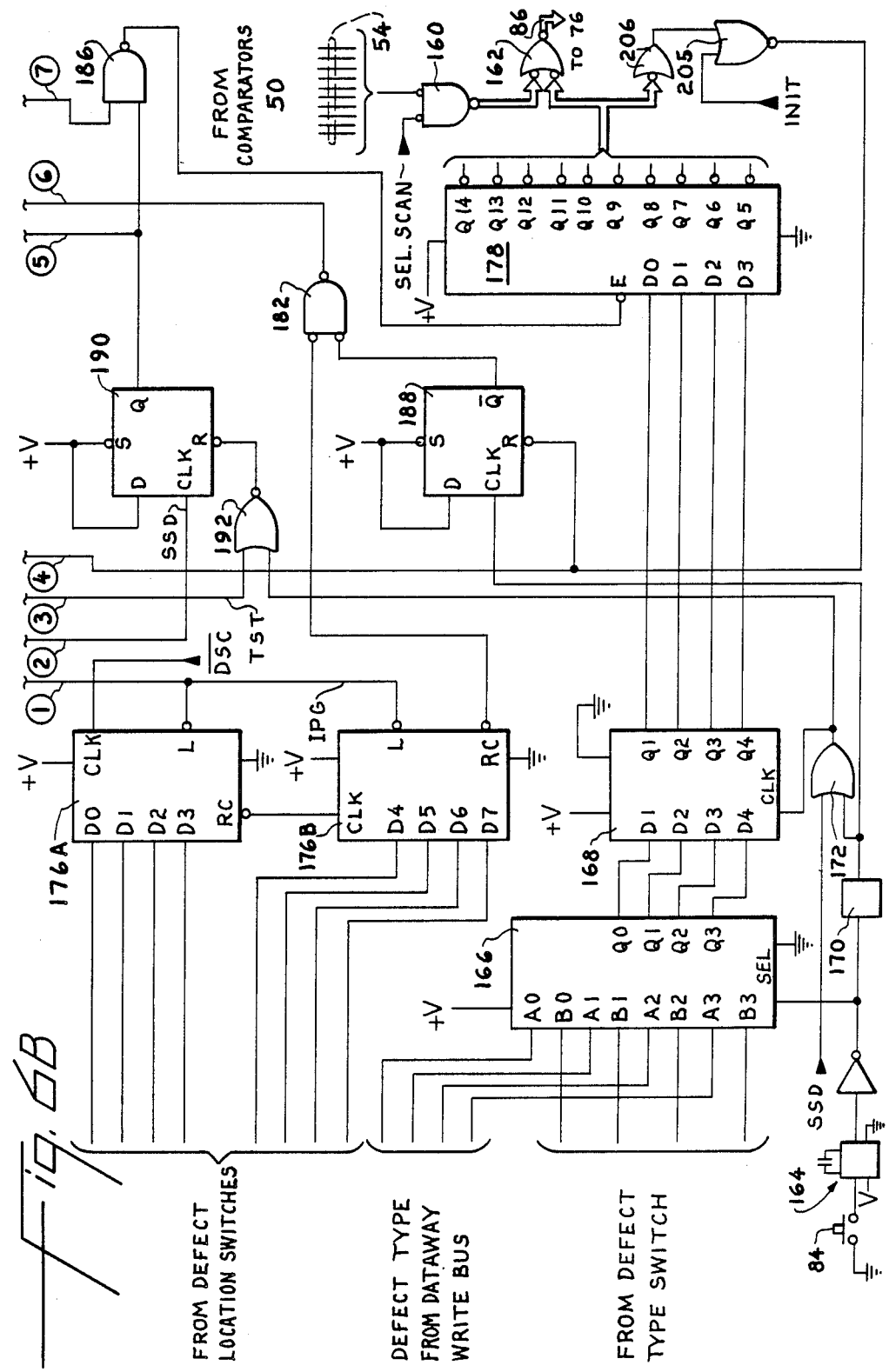

A detailed schematic diagram of the inspection bus interface module 74 is shown in FIGS. 6A and 6B. Referring to FIG. 6B, the output lines 54 from each of the comparators 50 are respectively connected to one input of a parallel array of gates 160. The actual discriminator firings representative of the presence of actually detected defects are gated through the gates 160 by the Selected Scan signal Sel. Scan derived in the manner discussed in connection with FIG. 2. The output of each of the gates 160 is gated through a parallel array of gates 162 onto the memory input bus 86 to the memory module 76.

Simulated defect signals selected by an operator or the host processor 72 (via the local processor 68) may be entered into the memory module 76 through the interface module 74.

The front panel includes three binary coded decimal thumbwheel switches 82 and an enter defect push button 84. As noted earlier, two of the switches ("Loc.", FIG. 3) define the lane in which the simulated defect is to appear. The third thumbwheel switch ("Type", FIG. 3) defines a type of defect to be generated.

When the enter defect push button 84 is depressed, the contact closure is debounced and inverted by the network 164 and applied to the control of a multiplexer 166. The multiplexer 166 passes the signals imposed by the defect type thumbwheel switch (applied at the "B" inputs of the multiplexer) to the inputs of a latch 168. The output of the debouncer network 164 is delayed by a delay line 170 and applied to the latch 168 through an OR gate 172 to latch the status of the defect type thumbwheel. Suitable for use as the multiplexer 166 is a device sold by, e.g., Texas Instruments under model number 74LS157 while the latch 168 is implemented by a device sold as model number 74LS174.

The status of the defect location thumbwheel switches is applied to the data inputs of a cascaded binary coded decimal down-counters 176A and 176B. Suitable for use as the counters 176 are devices sold by, e.g., Texas Instruments under model number 74LS190. The counters 176 are loaded by a low-going Internal Product Gate signal IPG. The counters 176 are decremented by the Simulated Defect Count signals DSC-NOT produced by the timing generator 80. It is recalled that the signal DSC-NOT transitions four hundred nanoseconds before the end of each lane.

The down-counters 176 count lanes and produce an output pulse when passing through zero, signalling that the spot 26 has reached the point along its scan path that is physically within the specified lane in which a simulated defect is to be placed. The ripple carry output (RC) signal from the counter 176B is applied through a control logic network to strobe a four-to-sixteen decoder 178. Suitable for use as the decoder 178 is a device sold by, e.g., Texas Instruments under model number 74LS154. The decoder 178 decodes the output of the defect type latch 168. The output of the decoder 178 appears as a pulse on the appropriate one of a plurality of output lines each of which is connected as the other inputs to a respective one of the parallel array of gates 162. Since the location of the simulated defect is specified by a lane number, rather than by an absolute location measured with respect to the web leading edge, the insertion of simulated defects is independent of the lane boundary family selected by the host processor 72.

The control logic network includes a gate 182 (FIG. 6B) the output of which is connected to a gate 184 (FIG. 6A). The gate 184 is itself connected to a NAND gate 186 (FIG. 6B) which enables the decoder 178. The gate 182 is opened by a low signal on the Q-NOT output of a flip-flop 188 produced when that device is clocked by the signal from the delay 170. The gate 186 is opened by a logic high on the Q output of a flip-flop 190. The flip-flop 190 is reset by the output of the gate 172 through a NOR gate 192. Suitable for use as the flip-flops 188 and 190 are devices sold by, e.g., Texas Instruments under model number 74LS74.

Simulated defects are entered by the local processor 68 in a similar fashion. The local processor 68 drives the appropriate address and function lines (A3) (F16) followed by a sixteen bit data word output on the write control bus of the Dataway. These address and function signals produce the Select Simulated Defect signal SSD on the Dataway interface module 78 (See FIG. 7A). The lower order bits of the data word are stored in the location latches 194 and specify where the defect is to appear in terms of system clock counts starting from the leading edge L of the scan path 30. The upper order bits of the data word are stored in the defect location latches 176 used when entering defects from the front panel. This operation can occur only if the front panel defect push button 84 is not depressed, insuring that the multiplexer 166 selects as its output the signals derived from the most significant bits of the data word provided by the local processor 68 on the Dataway.

The defect position signals are latched into the latches 194 by the action of the Select Simulated Defect signal SSD produced by the Dataway Interface module 78 and applied through an OR gate 196. Suitable for use as the latches 194 are devices sold by, e.g., Texas Instruments under model number 74LS174. The contents of the defect location latches 194 are loaded by the low-going Internal Product Gate signal IPG into cascaded binary down-counters 198A, 198B and 198C. Suitable for use as the counters 198 are devices sold by, e.g., Texas Instruments under model number 74LS191. The counters 198 are counted down by system clock pulses CLK gated through an AND gate 200 by the signal IPG. When the counter 198C reaches zero the ripple carry output (RC) sends a pulse through the control logic to strobe the decoder 178. Again, a pulse is produced on the output line from the decoder 178 specified by the defect type. The control logic permits only one defect to be generated for each entry from the local processor or from the front panel. The ripple carry output (RC) from the counter 198C is gated through a gate 202 and the gates 184 and 186 to the decoder 178. The gate 202 is opened by a low signal on the Q-NOT output of a flip-flop 204. The flip-flop 204 is clocked by the Select Simulated Defect signal SSD which places the gate 202 in the appropriate state. Suitable for use as the flip-flop 204 is a device sold by, e.g., Texas Instruments as model number 74LS74.

In the case of either operator or host processor-imposed simulated defects, a signal on any output line from the decoder 178 is gated through a multiple input NOR gate 206 (FIG. 6B). The output of the gate 206 resets the flip-flops 188 and 204 via a gate 205, readying these devices for the next imposition of simulated defects on the system. These flip-flops are also cleared through the gate 205 by the signal INIT.

The Inspection Bus interface module 74 also responds to Timing System Test signals TST. The local processor 68 enters the desired location of a Timing System Test signal TST in terms of lane location by driving the lower bits of the write control bus of the Dataway 70 with the desired location for the signal in system clock counts starting with the leading edge L of the scan path and also with the appropriate function and address signals to generate the TST signal. The count output from the processor 68 is latched in the latches 194 by the action of the TST signal through the gate 196 and down counted by the counters 198 by the CLK signal gated through the gate 200. The occurrence of counter underflow from the counter 198C will causes a Timing Test Done signal TTD to be produced. This signal is applied to the status register arrangement disposed within the Dataway interface module 78. This ripple carry output (RC) of the counter 198C is gated through a gate 208 (FIG. 6A) the output of which is gated through an AND gate 210. The gate 208 is opened by a low signal on the Q output of a flip-flop 212. The appropriate logic state of the flip-flop 212 is produced by the reset action of the Timing System Test signal TST through an inverter 214. Suitable for use as the flip-flop 212 is a device sold by, e.g., Texas Intruments under model number 74LS74. The AND gate 210 is opened by the Q output of the flip-flop 190. The flip-flop 212 is clocked by the fed back Timing Test Done signal TTD acting through an inverter 216.

DATAWAY INTERFACE MODULE

The Dataway interface module 78 is shown in the detailed schematic diagrams of FIGS. 7A, 7B, 7C and 7D. The portion of the Dataway interface module shown in FIGS. 7A and 7B generates all of the functional decodes needed to control the operation of the data compression interface 20. The details of the Dataway timing are provided in the IEEE CAMAC Standard 583 (1975) and appropriate appendices and amendments, hereby incorporated by reference herein. The portion of the Dataway interface module 78 shown in FIGS. 7C and 7D contains the status register arrangement.

Figure 7B:
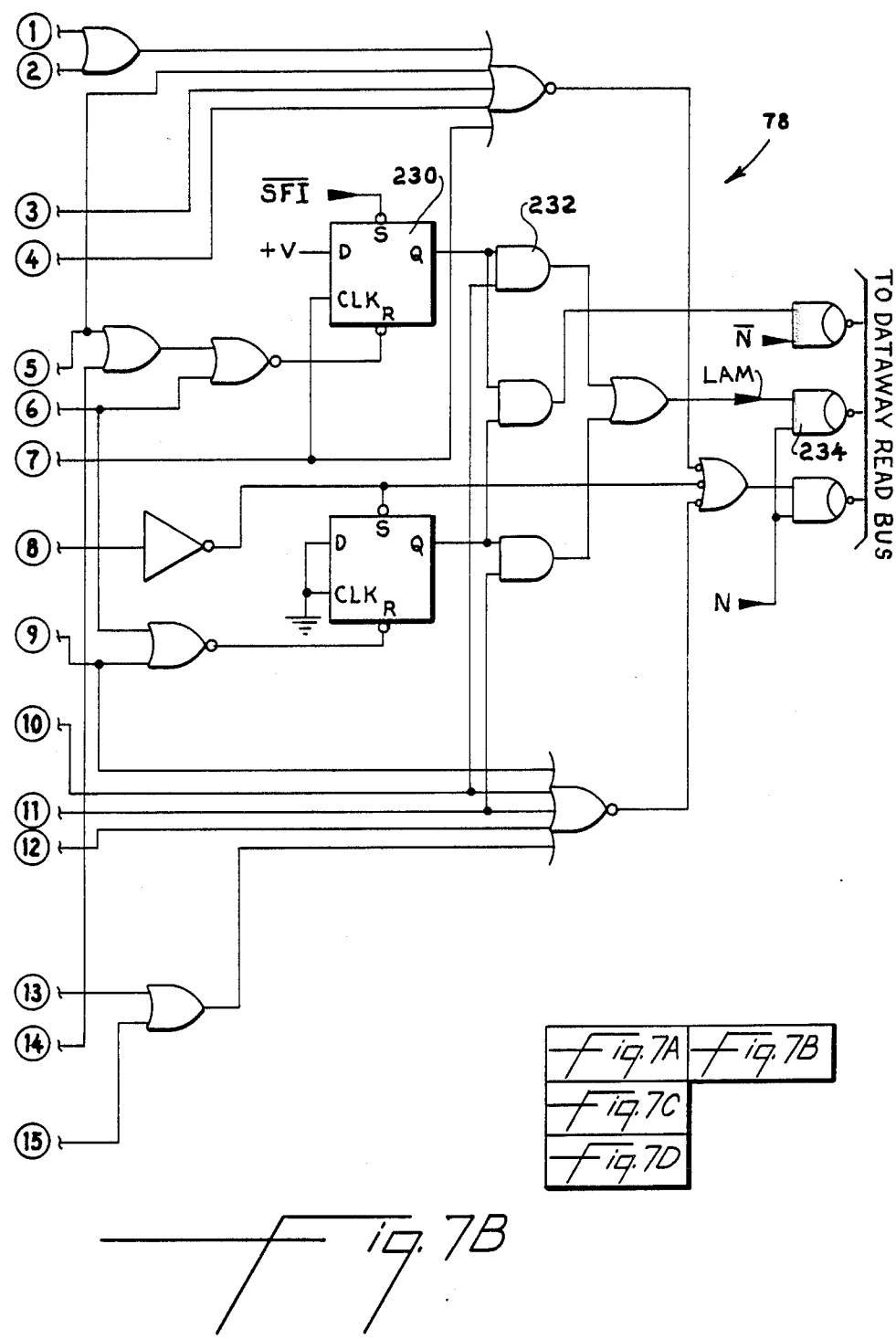

Referring to FIGS. 7A and 7B, complements of the signals on the address lines A1, A2, A4 and A8 of the Dataway address bus are connected to a decoder 224. Similarly, complements of function lines F1, F2, F4, F8 and F16 of the Dataway function bus are connected to a decoder 226. Suitable for use as each of the decoders 224 and 226 are devices sold by, e.g., Texas Instruments under model number 74154.

The output of the decoders 224 and 226 are applied to signal generation logic generally indicated by reference character 228 along with signals derived from the complements of the timing lines N, S1, S2 and Z of the Dataway 70.

Figure 7C:
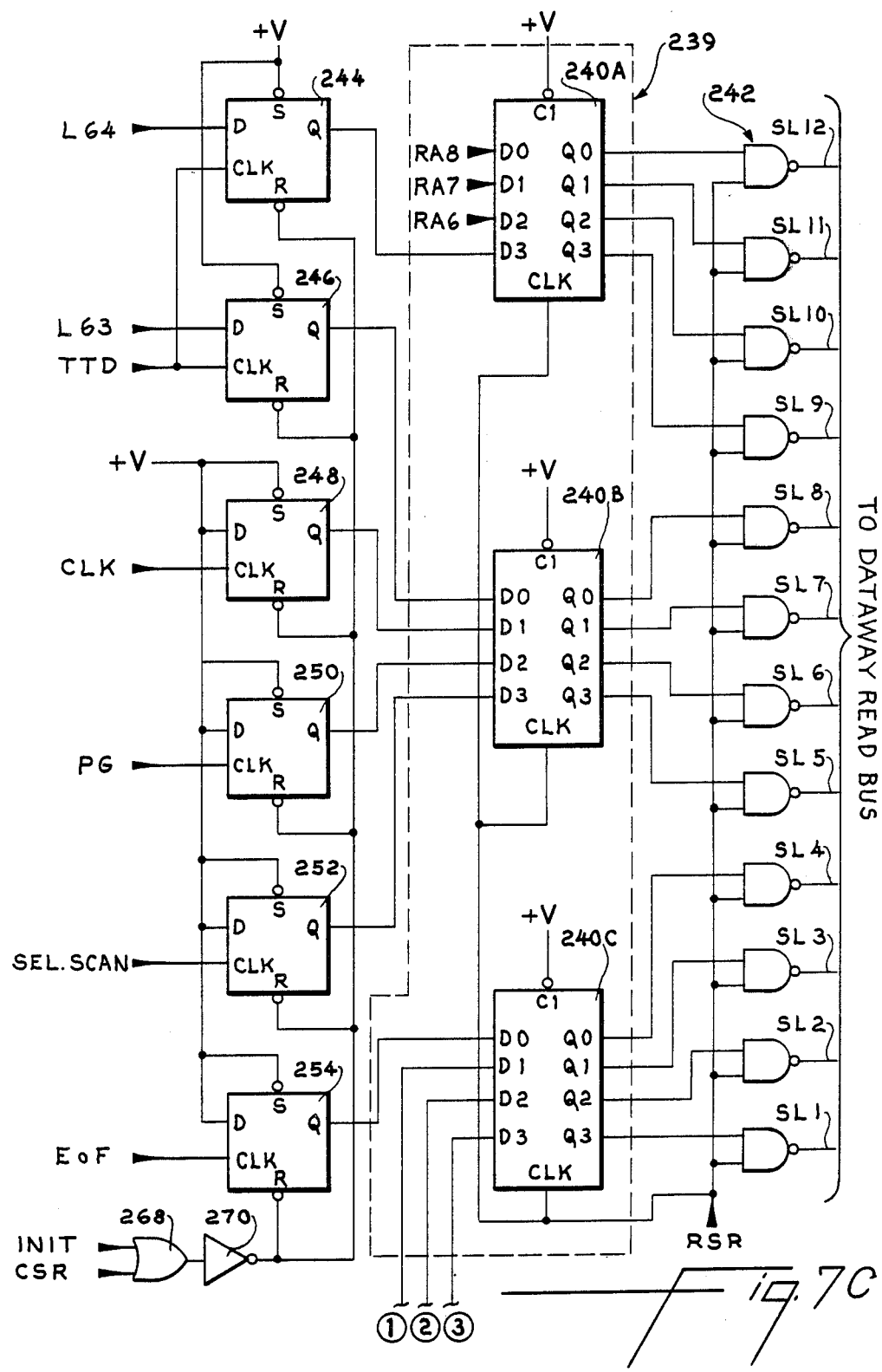

The signal on the address line AO and the signal on the function line FO are negative AND-ed to produce the interface control signal Read Status Register (RSR). This signal is applied as an enable to read the contents of the status register latches discussed in detail in connection with FIG. 7C. The signals on the address line AO and the function line F9 are similarly negative AND-ed to produce the interface control signal Clear Status Register (CSR) which clears certain of the latches as shown in FIG. 7C.

The signals on the address line A4 and the function line F16 are negative AND-ed and then combined with the signal on the timing line S1 to produce the Timing System Test signal TST which is used on the Inspection Bus interface module 74 (FIG. 6A) to enable the entry of the lane location of the Timing System Test signal.

The signals on the address line A1 and the function line F16 are negative AND-ed and combined with the signal on the timing line S1 to produce the Select Lane Family signal SLF which is applied to the timing generator module 80 shown in FIG. 4A. The SLF signal is used to enable the selection of the lane size family as determined by the host controller.

The signals on the address line A3 and the function line F16 are negative AND-ed and the signal so produced is combined with the signal on the timing line S1 to produce the Select Simulated Defect signal SSD. This signal is applied to the Inspection bus interface module 74 (FIG. 6A) and is used to enter simulated defects under the control of the host processor 72.

Figure 9B:
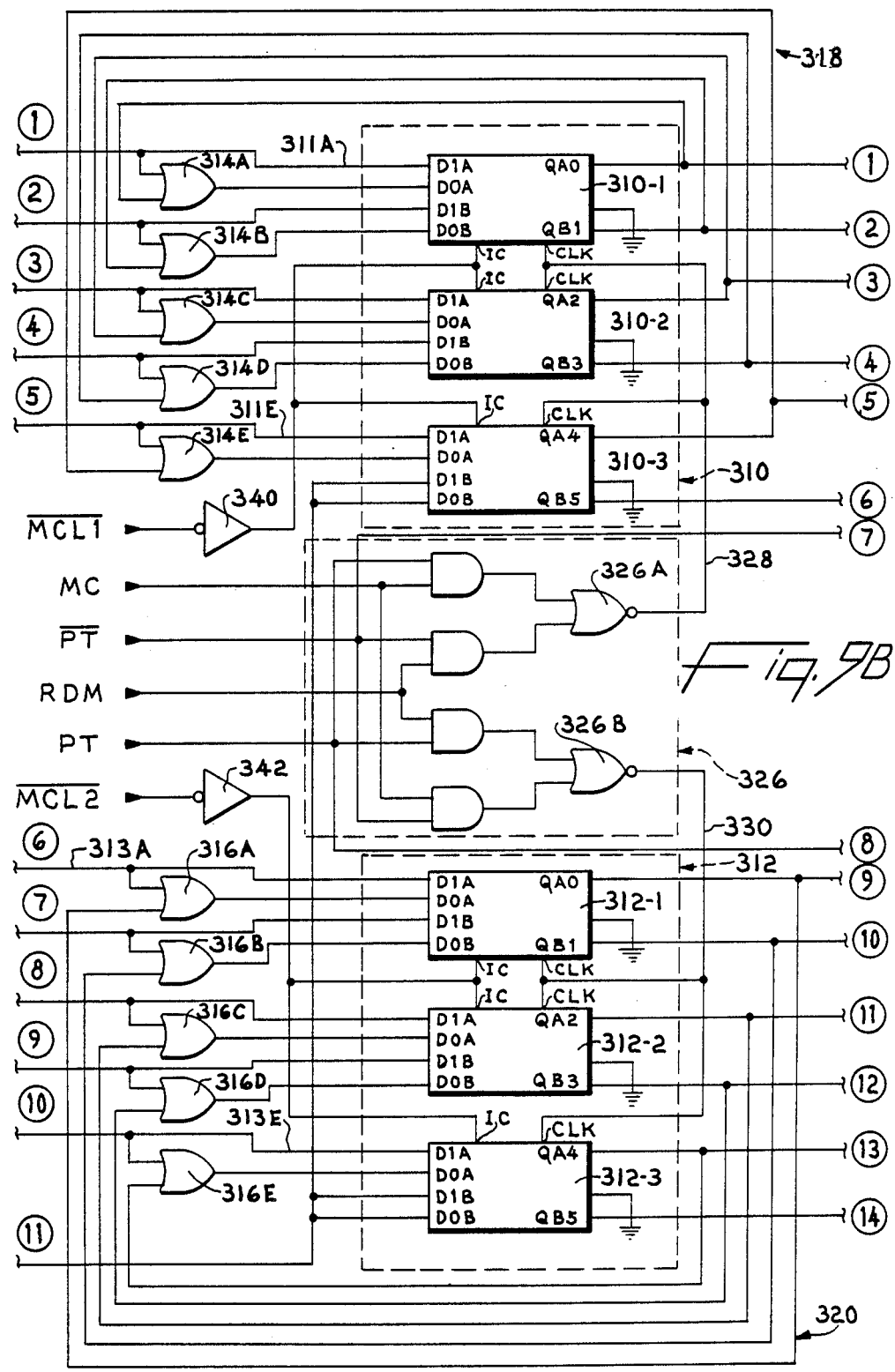

The signals on the address line A2 and the function line FO are negative AND-ed to produce the signal Enter Data (ED) which is used to transfer lane data from the memory module 76 to the Dataway read bus. The Enter Data control signal ED is itself negative AND-ed with the signal on the timing line S2 to produce the signal Read Memory (RDM) which is used as the output clock by the memory selector network 326 of the memory module (FIG. 9B). If the data compression interface 20 is used in a polled I/O system the local processor 68 will strobe the appropriate address, function and timing lines to produce the Enter Data signal ED and the Read Memory signal RDM. The timing relationship of these signals is determined by the CAMAC Standard.

Alternatively, the data compression interface 20 may be used to generate an interrupt to notify the local processor 68 that information is ready to be read onto the Dataway. In this instance, the complement of the Synchronized Frame Increment pulse SFI-NOT from the timing generator module 80 sets a flip-flop 230 (FIG. 7B, such as a device sold by, e.g., Texas Instruments as model number 74LS74). The Q output of the flip-flop 230 is gated through an AND gate 232 onto the Dataway read bus through an AND gate 234 opened by the signal on the timing line N. The local processor 68 is thus alerted that data is ready to be read. The data compression interface 20 responds by forming sixty-four Enter Data ED and Read Memory RDM signals, as discussed above, to read the data from the memory. Various associated signals needed in an interrupt system are generated by the Dataway interface module 78 as shown in FIGS. 7A and 7B.

In addition to the above, the complements of the signals on the timing lines S2 and Z are negatively AND-ed by a gate 236 to produce the system initialize signal INIT. This signal is inverted by the gate 238 to produce the complementary signal INIT-NOT. These signals are used to initialize the entire data compression interface 20 upon start-up.

Figure 7D:
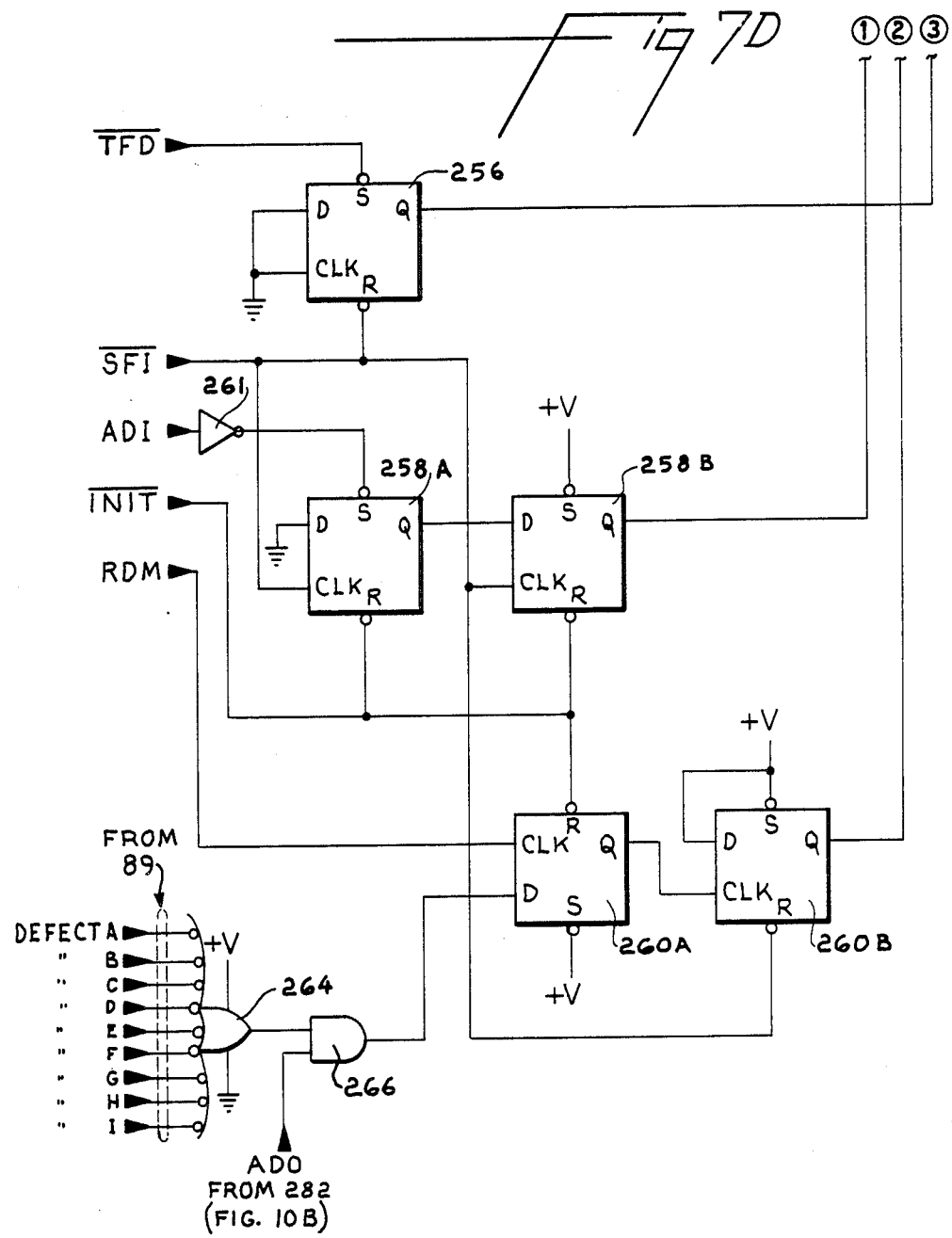

As seen in FIGS. 7C and 7D, the status register arrangement 239 includes an array of latches 240A, 240B and 240C. The outputs of these latches 240 are connected to the Dataway read bus through an array of NAND gates 242. The latches 240 are strobed and the gates 242 are opened by the assertion of the Read Status Register signal RSR decoded from the signals on the address line AO and the function line FO as discussed in connection with FIGS. 7A and 7B. Suitable for use as the latches 240 are devices sold by, e.g., Texas Instruments under model number 74LS175.

Three of the inputs to the latch 240A are derived from the three most significant bits of the lane size family address, viz., the signals RA8, RA7 and RA6, applied by the local processor 68 to the timing generator module 76 (FIG. 4A). These signals are latched into the latch 240A and are applied to the local processor as Status Lines SL12, SL11 and SL10, respectively.

The other of the inputs to the latches 240 are derived from the output of flip-flops 244 through 260. Suitable for use as each of these flip-flops is a device sold by, e g., Texas Instruments under model number 74LS74.

Status line SL1 is asserted through the flip-flop 256. The flip-flop 256 is set by the complement of the Transfer Done signal (TFD-NOT) produced when defect information is transferred from the memory to the local processor 68 (see FIG. 9C). This flip-flop is cleared at the end of a frame by the complement of the Synchronized Frame Increment signal SFI-NOT.

Status lines SL2 and SL3 are derived from the register arrangement 260 and 258, respectively. The application of a characteristic signal to the serial memory (or latch) selected as the input memory (or latch) produces the Any Defect In signal (ADI) which is generated by the gate 282 in the memory module 76 (FIG. 10B). The complement of this signal, ADI-NOT, from the inverter 261 sets the flip-flop 258A placing a logic high at the Q output thereof. The signal SFI-NOT produced at the end of the frame in which the signal ADI is generated clocks the flip-flop 258B thus placing a logic high signal at the Q output thereof which is loaded into the latch 240C by the Read Status Register signal RSR. This signal provides a first status signal representative of the application of a characteristic signal (on SL3) to the memory (or latch) selected during a frame. The flip-flops 258 are reset by the pulse INIT-NOT.

If in the next subsequent frame a signal is read from the serial memory (or latch) onto the Dataway read bus the output of the gate 264 goes to a logic high. The inputs to this gate are derived from the signals on the bus 89 branching from the memory output bus 88. This signal is gated through an AND-gate 266 to the data input of the flip-flop 260A. The gate 266 is opened by the Any Defect Out signal ADO carried on the line 299-56 from the multiplexer 298 (FIG. 10B). The memory output clock signal Read Memory RDM clocks the flip-flop 260A. This sets the Q output of the flip-flop 260A to a logic high, which in turn clocks the flip-flop 260B to apply a signal to the latch 240C. In this manner a second status signal representative of the transmission of information out of the memory (or latch) which served as the input memory (or latch) during the preceding frame is generated (on SL2) permitting a monitorable indication of the operability of that memory (or latch). The flip-flop 260A is reset by the INIT-NOT signal and the flip-flop 260B is reset by the signal SFI-NOT.

Status Lines SL4 through SL7 are derived from the flip-flops 254, 252, 250 and 248, respectively. These devices have their respective clock inputs tied to the timing signals End of Frame (EoF), Selected Scan (Sel. Scan), Product Gate (PG) and CLK carried on the Inspection Bus 49. These flip-flops will be set if these signals are active. These devices (as well as the flip-flops 244 and 246) are cleared by the Clear Status Register signal CSR derived as shown in FIG. 7A and applied through the OR gate 268 and the inverter 270. The flip-flops 244 through 254 are initially reset by the signal INIT applied through the same gates.

Status Lines SL8 and SL9 are derived from the flip-flops 246 and 244, respectively. The flip-flops 244 and 246 are clocked by the Timing Test Done signal TTD produced by the Inspection Bus interface module 74 (FIG. 6A). The data lines of these devices are driven respectively by the L64 and L63 signals produced on the timing generator module 80 (FIG. 4A). If a Timing Test signal TST is mandated by the local processor 68 to occur in lane sixty-four, for example, and if the Timing Test Done signal is generated in lane sixty-three, the flip-flop 246 is set so that the local processor 68 may be appraised of a timing system discrepancy in the data compression interface 20 by the appearance of the signal on the line SL8. If in this example the Timing Test Done signal is generated during lane sixty-four, the flip-flop 244 is set, indicating to the local processor 68 that the timing system is properly functioning by the appearance of the signal on the line SL9.

In this manner the overall design philosophy of the self-check features of the interface 20 may be realized. The host processor 72 may monitor the operation of each of the modules that comprise the data compression interface 20 and fully test each module while the interface 20 is functioning on-line.

MEMORY MODULE

Figure 9C:
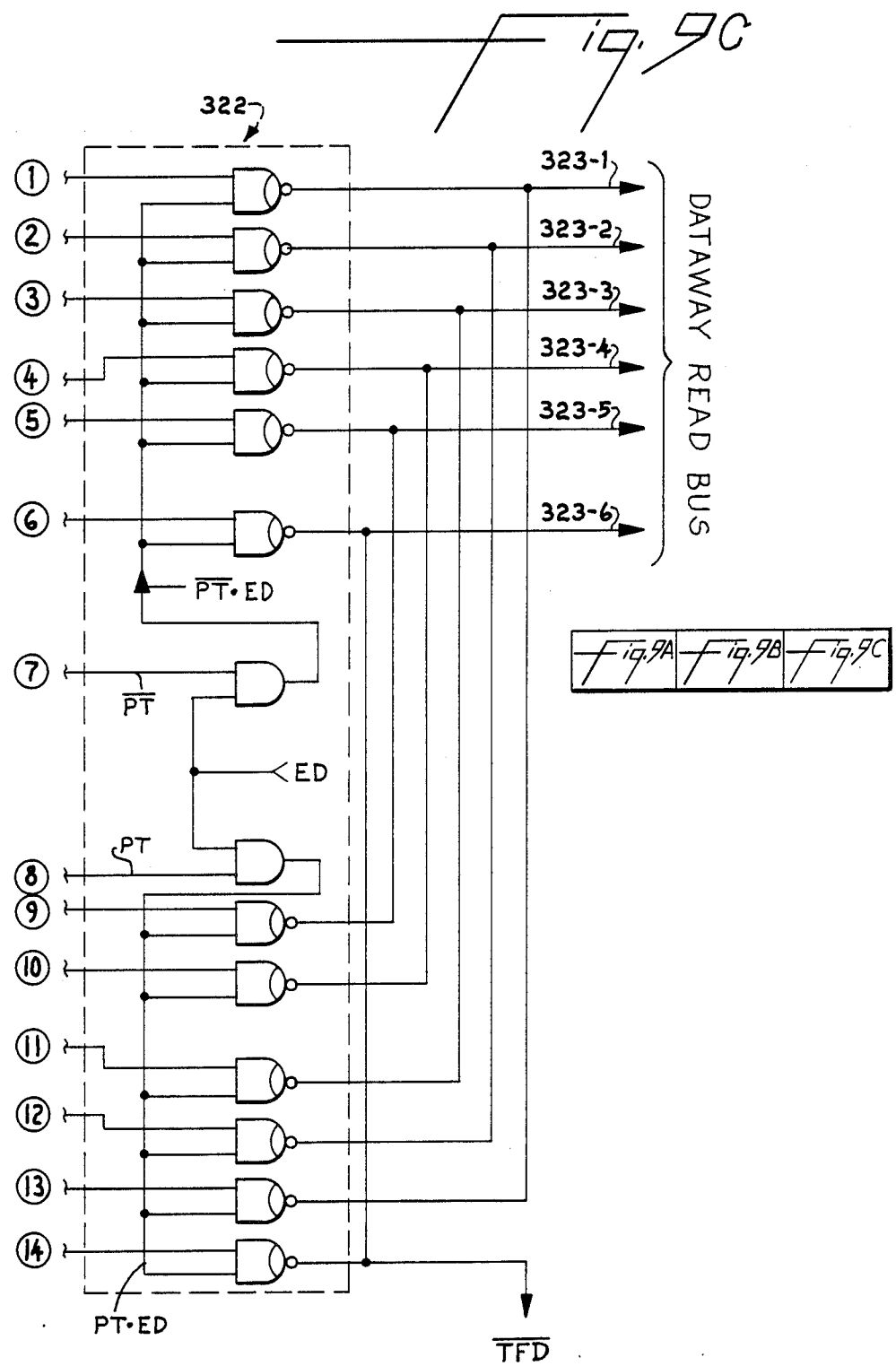
Figure 10A:
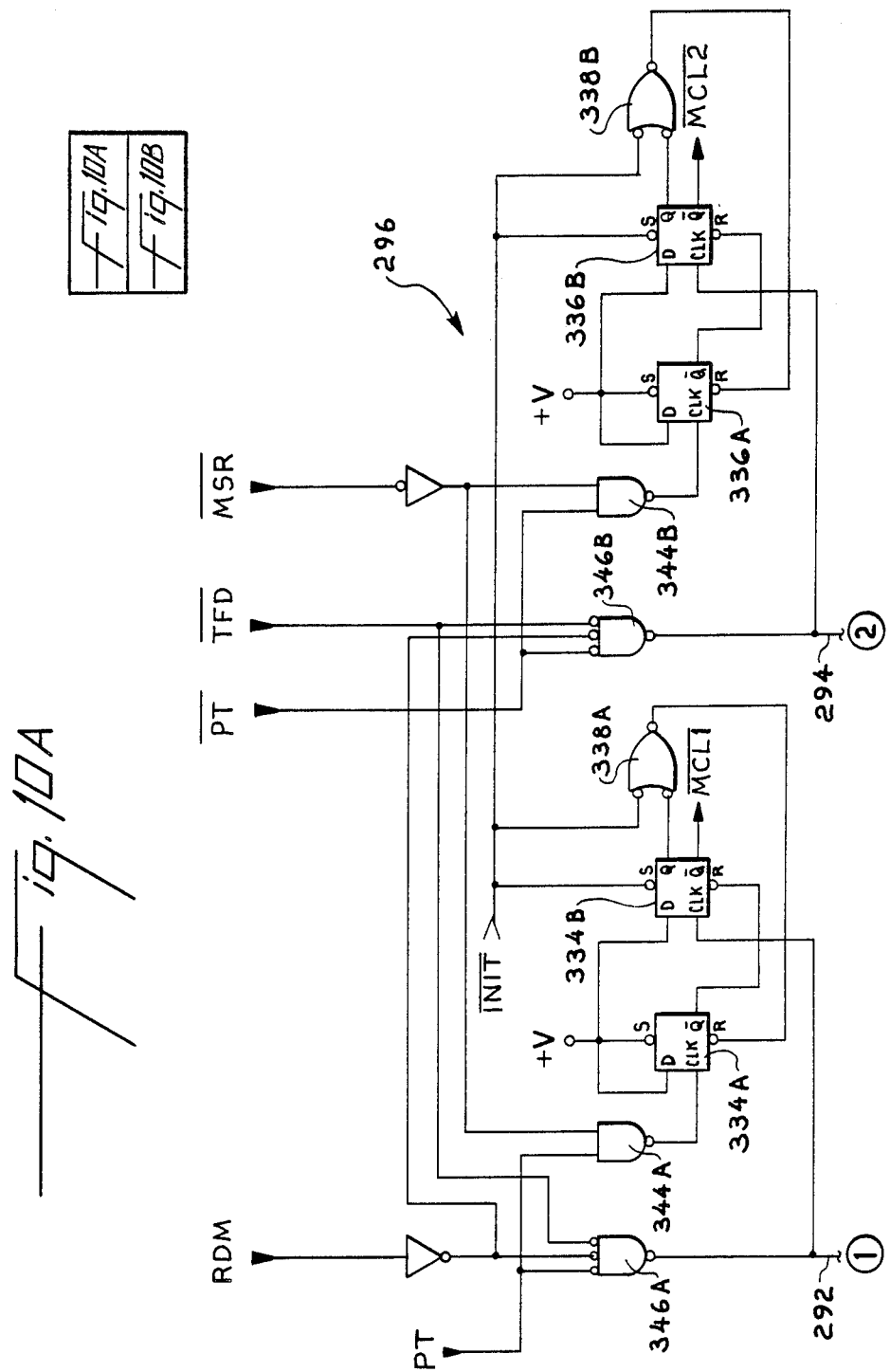

The architecture of the memory module used in the data compression interface 20 in accordance with the present invention is shown in FIGS. 8, 9 and 10. FIGS. 8A and 8B are a functional block diagram of the memory module 76, while FIGS. 9A, 9B and 9C are detailed schematic diagrams of the portion of the memory module 76 used to store and produce an accumulated lane-by-lane summary of the lane-oriented defects. FIGS. 10A and 10B are detailed schematic diagrams of the portion of the memory module 76 used for nonlane-oriented defects.

The outputs of the comparators 50 (whether triggered by real or simulated defects) are applied in the form of pulses to the memory system module 76 from the Inspection Bus interface module 74 over the memory input bus 86. Within the memory module 76 the memory input bus 86 bifurcates to the nonlane-oriented defect memory section (FIGS. 8B, 10) and the lane-oriented defect memory section (FIGS. 8A, 9).

With respect to the nonlane-oriented defects, signals representative of Defects F through I and the Any Defect In signal ADI (the logical sum (OR) of all defects derived from a multiple input gate 282) are applied to a data director logic network 284 (FIG. 10B) configured from an array of NAND gates. The output of the network 284 is applied to two storage latch networks generally indicated by reference characters 288 and 290 connected in parallel. One of the latch networks is selected as the input or data collection latch network and the other as an output latch network in accordance with the state of enabling signals PT or PT-NOT applied to the data director network 284 in conjunction with latch control signals from a latch control network 296.

Data is read into the latch network selected as the input latch in accordance with control signals applied over lines 292 or 294 from the latch control network 296 (FIG. 10A). These control signals are generated in response to the Pointer signal PT, the complement of the Transfer Done signal TFD-NOT and the memory output clock signal Read Memory RDM to set the latch networks to receive and store nonlane-oriented defect characteristic signals. The network 296 is also responsive to the complement of the Memory Select Reset signal MSR-NOT and the Pointer signal PT to generate the complements of the Memory Control signals MCL1-NOT and MCL2-NOT used in the lane-oriented defect memory section (FIGS. 8A, 9B). Since there is no lane information associated with nonlane-oriented defects the occurrence of a such a defect anywhere within a frame will cause a bit to be set in a corresponding latch in the asserted storage latch network. The appropriate latch network is asserted by the data director 284 and the control logic 296. The latch will remain set until the information is transferred to the local processor 68.

The output from each of the storage latch networks 288 and 290 is applied onto the Dataway read bus over the memory output bus 88 via a multiplexer/driver 298. The multiplexer 298 is configured from an array of NAND gates (FIG. 10B) and is operated in accordance with the state of the Pointer PT signal and the Enter Data signal ED. Suitable for use as the gates 298 are devices such as those sold by, e.g., Texas Instruments under model number 74LS38. The memory output bus 88 (including the Any Defect Out signal ADO) is also connected by a bus 89 to the Dataway interface module 78 (FIG. 3). A signal on any of the output lines 299-1 through 299-4 represents the occurrence of defect type F through I respectively along any scan path in the frame. The signal on the line 299-5 is the Any Defect Out signal ADO. The output lines 299 from the gates 298 are read by the processor 68 together with the outputs from the serial memories, as discussed herein.

With reference to FIG. 10A, the latch control network 296 includes two pairs of flip-flops 334A and 334B and 336A and 336B. Suitable for use as these flip-flops are devices sold by, e.g., Texas Instruments as model number 74LS74. The reset pins of the flip-flops 334A and 336A are respectively connected to the output of gates 338A and 338B. The Q-NOT output of these flip-flops reset the flip-flops 334B and 336B. The Q-NOT output of the flip-flops 334B and 336B is applied, via the inverters 340 and 342 (FIG. 9B), as the Memory Control signals MCL1 and MCL2 to the serial memories 310 and 312, respectively. The flip-flops 334A and 336A are clocked via the outputs of NAND gates 344A and 344B. The flip-flops 334B and 336B are clocked via the gates 346A and 346B.

As seen in FIG. 9A lane oriented defects from the memory input bus 86 are applied to a data collection register 302. The register 302 is configured from an array of flip-flops such as those sold by, e.g., Texas Instruments as model number 74LS74. The register 302 is enabled by the logical product of the Internal Product Gate signal IPG and the complement of the Buffer Gate Signal BG-NOT produced by an AND gate 304. The occurrence of a characteristic signal representative of a defect on any of the input lines is stored in the corresponding flip-flop in the data collection register 302 until the end of the lane. Thereafter, a plurality of parallel bits (one bit for each of the defect types) which occurred during that lane is transferred from the flip-flops in the register 302 to corresponding flip-flops in a buffer register array 306 through an array of NAND gates 308. The gates 308 are enabled by the Buffer Gate signal BG. The registers 306 (similar to the registers 302) are clocked by the complement of the Lane Boundary signal LB-NOT.

The output of the buffer register 306 is directly applied to the inputs of two serial memories 310 and 312 (FIG. 9B) over lines 311 and 313 respectively. The serial memories 310 and 312 are connected in parallel. In addition, the outputs of the buffer register 306 are applied to one data input of an array of logic gates 314 and 316 respectively associated with each of the memories 310 and 312. The other input of the OR gates 314 and 316 is derived in a feedback loop 318 or 320 from the recirculated output of the serial memory with which it is associated. The outputs of the serial memories 310 and 312 are connected to a multiplexer/driver 322 which in turn is applied to the output memory bus 88.

A memory selector logic network 326 (which includes a gate 326A and a gate 326B) is responsive to the memory input clock signal MC derived by the timing generator module 80, and the memory output clock signal Read Memory RDM decoded by the Dataway interface module 78 to respectively load data into or read data from the serial memory asserted by the selector network 326 as the input (data collection) or output memory during a given frame. The data collection and the output memory functions are alternately assigned to the memories 310 and 312 by the selector network 326 in accordance with the states of the Pointer signal PT and its complement PT-NOT. Appropriate input clock signals MC or output clock signals RDM are applied to the memory selected as the input or output memory, as the case may be, via lines 328 and 330.

The serial memories 310 and 312 are each formed from serial memory elements such as shift registers manufactured and sold by, e.g., Texas Instruments under model number TDC1005J. The shift registers each contain two banks of sixty-four storage locations or stages. The number of storage locations in each serial memory element corresponds to the number of lanes into which each scan path is electrically subdivided. Each bank of storage locations in a memory element is reserved for a particular lane-oriented defect type. Thus, in the specific embodiment depicted, each of the parallel-connected serial memories 310 and 312 comprises three serial memory elements 310-1, 310-2, 310-3 and 312-1, 312-2, 312-3. Each memory 310 and 312 can thus accommodate five lane-oriented defect types (Defects A through E, respectively) and a Transfer Done bit discussed herein. Of course, further memory banks may be provided to accommodate more defect types, if desired.

Each serial memory 310 or 312 is also responsive to a Memory Control signal MCL1 or MCL2 derived from the latch control logic 296 (FIG. 10A) which is asserted during the first data collection scan path in each data collection frame. The memory control signal MCL asserts that input port of each serial memory element which is directly connected to the lines 311 or 313 from the output of the buffer register 306, thereby bypassing the OR gates 314 or 316. Thus, during the first scan in any data collection frame the memory selected as the data collection memory receives its inputs directly from the buffer register 306 without passing through the associated logic gates 314 or 316. During each of the other scan paths in the frame the memory control signal MCL is not asserted and information is thus recirculated from the output stage of the selected serial memory to the input of its associated logic gates.

During scan paths subsequent to the first in a data collection frame each characteristic signal generated during the current scan path is logically summed with the accumulated lane-by-lane characteristic summary stored in the last stage of the serial memory and recirculated over the bus 318 or 320. Because each serial memory bank has the same number of stages as there are lanes across the scan path the information present in the last stage of the memory was loaded thereinto during the same lane of a previous scan path as the data detected and presented to the gate 314 or 316 during the present scan path. Thus, a bit set in an output stage of a bank of the serial memory will always correspond to the occurrence of a defect in the lane just completed on a current scan path. The characteristic signal in the buffer register will always represent the occurrence of a defect during the same lane of the current scan path. When these two signals are logically summed and applied to the input of the serial memory the occurrence of a defect will set a bit in the serial memory which will remain set until read by the local processor. It may thus be appreciated that an accumulated lane-by-lane summary of lane-oriented defect information may be generated by the serial memory selected as the data collection memory during a current frame.

The serial memory designated as the output memory by the memory selector network 326 transfers its contents to the local processor 68 over the memory output bus 88 to the read bus of the Dataway 70. The signals on the lines 323-1 through 323-5 from the output of the multiplexer/driver 322 carry an accumulated lane-by-lane summary of the occurrence of defects A through E respectively derived from their associated memory banks. The signal in the line 323-6 is the Transfer Done Flag bit. The memory output bus 88 is formed of the lines 323-1 through 323-6 taken together with the lines 299-1 through 299-5 from the nonlane-oriented defect memory section. These lines are connected to the Dataway read bus. The output of each bank of serial memory 310 or 312 and of each latch 288 or 290 is read in parallel by the local processor 68. The accumulated lane by lane summary of each lane-oriented defect is transferred in parallel, lane bit by lane bit, to the processor 68 in accordance with the Read Memory signal RDM. At the occurrence of each Read Memory signal RDM the contents of each serial bank is shifted onto its respective output line 323 to the Dataway Bus 70. As seen from FIG. 11, which is a compilation of the block of defect information (both lane-oriented and nonlane-oriented) transmitted to the local processor, information regarding the occurrence of each defect type A through E in lane 1 is transmitted first, followed by information regarding the occurrence of each defect type A through E in lane 2, etc. The transfer continues until the Transfer Done flag bit (a logic zero on the line 323-6) is read by the local processor.

Figure 11:
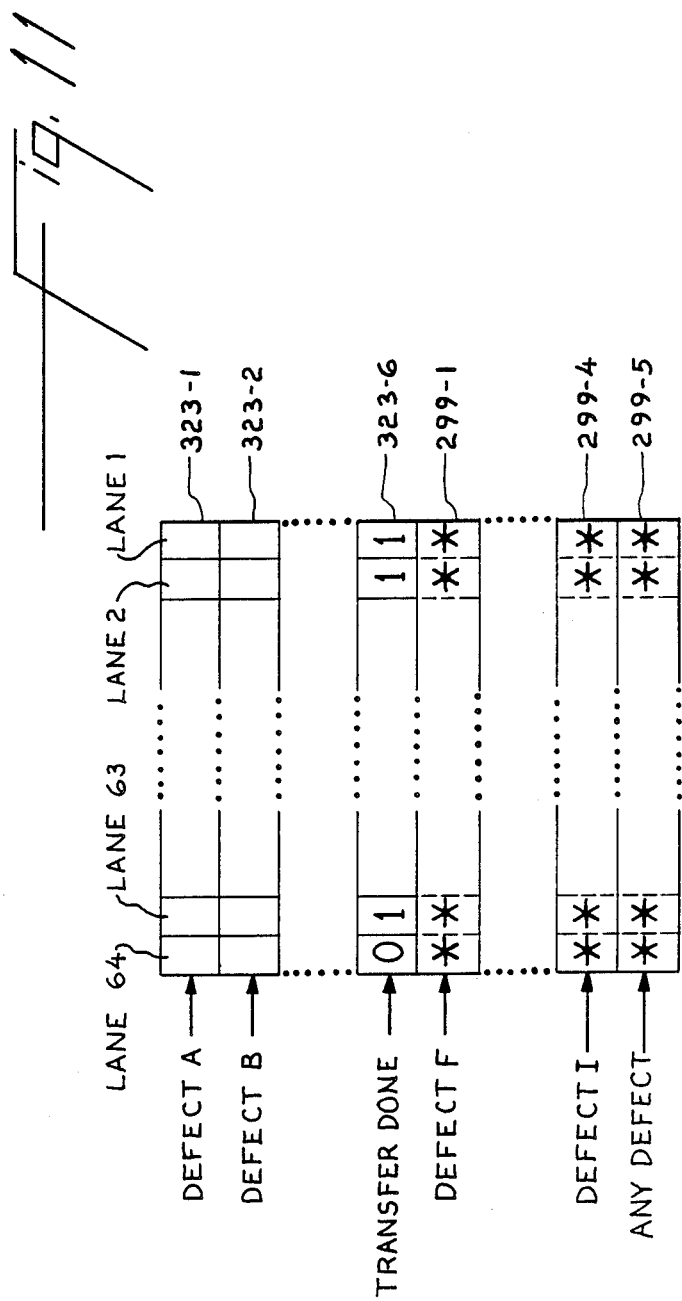
FIG. 11 is a representation of lane oriented and nonlane oriented summary data words transmitted from the data compression interface of the present invention to the Local Processor.

Since the nonlane-oriented defect information represents either the occurrence or nonoccurrence of such a defect in a frame the same signal is transmitted to the local processor 68 on the lines 299. However, as seen in FIG. 11, this may be envisioned from the point of view of the processor 68 as sixty-four transmissions (one for each lane) of the same data. This is denoted by the asterisks in FIG. 11 which indicate the same signal is on the line 299 each time the processor 68 reads that line. Since there is no true lane boundary for nonlane-oriented defects, the partitions in these summary words are shown as dotted lines.

In some instances, for lane-oriented defects, the stage corresponding to lane sixty-four may be used as a bit indicative of the presence of a particular defect in a frame. Thus, if a defect of a particular type is detected in any lane in a frame, the sixty-fourth memory stage in the bank corresponding to that defect is set. This provides a shortened way for the processor to ascertain the occurrence in a frame of a particular lane oriented defect.

After the last transfer the output serial memory and the output latch are then ready for use as a data collection or input memory or latch for a succeeding collection frame.

DETAILED DESCRIPTION OF THE MEMORY SYSTEM OPERATION

Figure 12:
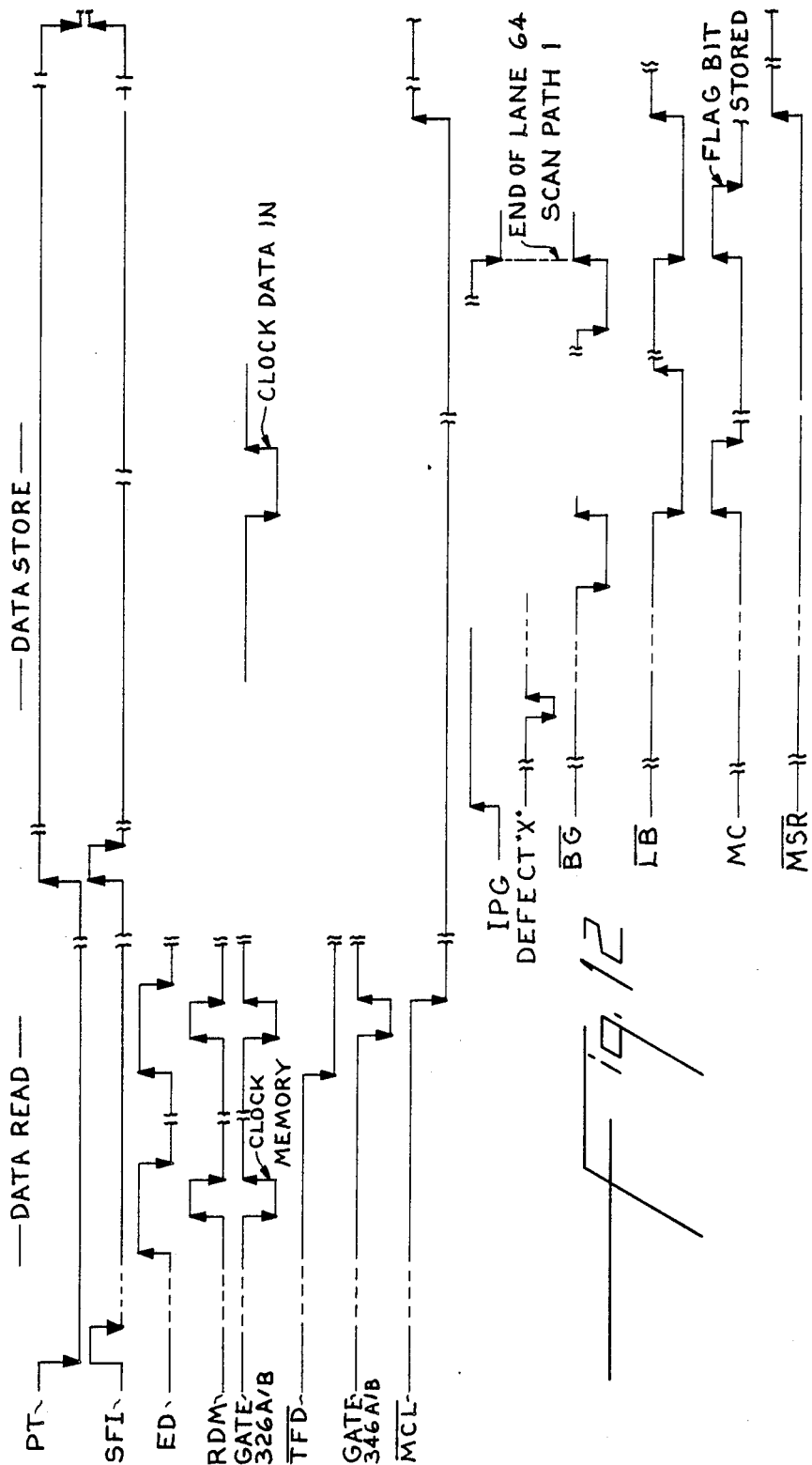
FIG. 12 is a timing diagram of the operation of the memory module of the present invention.

The description which follows may be best understood by reference to FIG. 12, which is a detailed timing diagram of the memory operation.

On system power up the local processor 68 ensures system initialization by the production of the initialize signals INIT and its complement INIT-NOT from the Dataway interface as earlier discussed. The INIT-NOT signal is applied to the memory module 76 and serves to reset the data collection registers 302, the buffer registers 306 and the storage latch networks 288 and 290. This ensures that no false defects are generated on system power-up. In addition, the signal INIT-NOT resets (forces high) the Q-NOT output of the flip-flops 334A and 336A in the latch control network 296 via gates 338A and 338B. INIT-NOT also sets (forces high) the Memory Control signals MCL1 and MCL2 derived from the Q-NOT outputs of the flip-flops 334B and 336B and applied to the control pins of the serial memories 310 and 312 via inverters 340 and 342, respectively. This insures that the inputs to the serial memory selected as the data collection memory will come directly from the output of the buffer registers 306 without being OR-ed with old data. (When INIT-NOT is terminated, the reset pins of the flip-flops 334A and 336A are released.)

In the data collection mode, characteristic signals are received by the Inspection Bus interface module 74 via gates 160 (FIG. 6B). These gates are used to gate the defect signals with the Selected Scan signal Sel. Scan to ensure that only new data is processed by the data compression interface. Actual defect signal data is combined with simulated data by gates 162 and the low-going defect signals (whether of real or simulated origin) are applied to the memory module 76 over the memory input bus 86.

During each scan path in a frame the lane-oriented defect signals (Defects A through E) are fed directly to the set pins of the data collection flip-flops 302. As seen from the timing diagram (FIG. 12) these flip-flops 302 will be set by a low level on their associated defect lines (e.g., by Defect X, FIG. 12) and will remain set until cleared by a logic zero being clocked into them from the gate 304. (The flip-flops 302 are cleared via the gate 304 by the Internal Product Gate signal IPG and the rising edge of the complement of the Buffer Gate signal BG-NOT which is coincident with the end of each lane.) Should a defect overlap two lanes the data collection flip-flop 302 will not be cleared (because the set function will override the clock signal) and will remain set during the following lane.

The output of the data collection flip-flops 302 is gated by the Buffer Gate signal BG through the NAND gates 308. The low true output of the gates 308 is applied to the set lines of the buffer flip-flops 306. The Buffer Gate signal BG will transition high four hundred nanoseconds prior to the end of the lane and will remain high until the end of the lane. If the data collection flip-flop 302 has been set during the lane or becomes set during this four hundred nanosecond period the buffer registers 306 will be set. At the end of the lane Buffer Gate signal BG falls (FIG. 12), blocking any further data transfers until the end of the next lane. At this time the outputs of the buffer registers 306 reflect the status of the data collection flip-flops 302 at the end of the previous lane. This data will be held until it is written into the serial memories. Data is written into the serial memories by the falling edge of the Memory Clock signal MC as inverted by the gate 326A or 326B, as the case may be. The registers 306 are cleared by the following rising edge of the complement of the Lane Boundary signal LB-NOT. The appropriate clock signals (i.e., input clock MC or output clock RDM) are routed via the gates 326A and 326B to the input and output memory respectively via the Pointer signal PT input to a memory selector logic network 326. The state of the signal PT or its complement PT-NOT results in one of the memories 310 or 312 being selected as the input or data collection memory while the other is selected the output memory.

During the first scan path in a frame the serial memory selected as the input memory receives a Memory Control signal MCL-NOT in a logic low state. The Memory Control signal MCL-NOT is derived from the flip-flop 334B or 336B in the latch control network 296 (FIG. 10A). After inversion by the appropriate inverter 340 or 342 (FIG. 9B) a logic high signal is applied to the serial memory selected as the input memory, thus permitting that memory to receive its inputs from the lines 311 or 313, i.e., directly from the buffer registers 306 and thus bypassing the logic gates 314 or 316. At the end of the first scan path, the Memory Select Reset signal MSR changes state (FIG. 4B), resetting the flip-flop 334B or 336B and terminating one of the Memory Control Signals MCL. Thus, during every other scan path in that frame, the serial memory is loaded with the logical sum of the characteristic signal and the recirculating memory signal.

During each scan path five bits representative of the presence of lane-oriented defects in the lane under consideration and a sixth bit (the Transfer Done flag bit) are input into the input memory in synchronism with the movement of the spot 26 along its scan path. The Memory Clock signal MC, applied to the input memory through the memory selector logic 326, controls the loading of lane data into the input memory and the shifting of data through the serial locations in each memory element. The Transfer Done Flag bit is generated from the output of the gate 304 via the inverter 324 and applied to the sixth memory bank. The Transfer Done Flag bit is a logic high when the Internal Product Gate signal IPG transitions at the end of the scan path. The Transfer Done Flag bit, when gated through the multiplexer/driver 322 onto the line 323-6 generates the complement of the Transfer Done signal TFD-NOT. This signal, when read by the local processor 68, terminates the transmission of data.

At the end of the data collection frame an End of Frame signal EoF is received via the Inspection Bus and is synchronized on the timing module to occur with the end of the last write operation in the scan. At this time the Pointer signal PT is inverted and selects the other serial memory as the input memory and the previous input memory as the output memory. Data is read from the output memory by the host processor through the Dataway 70 in accordance with the output clock Memory Read signal RDM asserted via the memory selector logic 326. The data is driven onto the memory output bus 88 via the multiplexer/driver 322, which is enabled by the logical product of the signals Pointer PT and Enter Data ED.

With regard to nonlane-oriented defects, the data director logic 284 enables one or the other of the latch arrays 288 or 290 (FIG. 10B). The appropriate latch associated with Defect-type F through I and Any Defect is set by the occurrence of such a defect in the frame. The Q output of the asserted latch is connected over the lines 299 from its multiplexer/driver 298 onto the memory output bus 88 by the action of the Memory Read signal RDM asserted via the gate 346A or 346B (FIG. 10A).

From the foregoing it may be appreciated that there has been provided a data compression interface having a streamlined memory architecture which permits information regarding both lane-oriented and nonlane-oriented defects to be collected and an accumulated lane-by-lane summary thereof produced, while such a summary that had been accumulated during a previous frame is asynchronously (with respect to data collection) transmitted to the local processor 68.

Those skilled in the art, having the benefit of the teachings of the present invention as hereinabove set forth may effect numerous modifications thereto. These modifications are to be construed as lying within the scope of the present invention, as defined by the appended claims.

What is claimed is:

1. An inspection system for inspecting a web subdivisible into a series of frames comprising:
   a flying spot generator for generating a flying spot of radiation movable over the web along a plurality of transverse scan paths, each frame comprising a predetermined plurality of scan paths each of which is subdivisible into a number of transversely contiguous lanes;
   a detector for generating a pedestal signal representing the radiation transmitted through or reflected by the web;
   a discriminator responsive to the pedestal for generating a characteristic signal representative of the presence of a predetermined physical property on the web at a corresponding lane of a scan path; and
   first and second serial memories connected in parallel, each memory having a number of stages corresponding to the number of lanes, one memory being selectable during alternate frames as an input memory for storing each characteristic signal in the stage corresponding to the lane in which it was generated to produce an accumulated lane-by-lane summary of the occurrence of the property during a frame, while the other memory is selectable as an output memory from which the summary produced during the preceding frame is read.

2. The inspection system of claim 1 wherein each memory is connected in a recirculating configuration with the memory output fed back to the input, the system further comprising:
   a logic network connected intermediate the discriminator and the input to each of the memories, the logic network deriving as its inputs the characteristic signal generated during the current scan path and the recirculating memory signal to apply to the input memory the logical sum of these two inputs.

3. The inspection system of claim 2 wherein
   the discriminator is responsive to the pedestal signal to produce a second characteristic signal representative of a second predetermined physical property on the web, and further comprising:
   a first and second storage latch connected in parallel, one latch being selectable during alternate frames as an input latch for storing the second characteristic signal to provide an indication of the occurrence of the second property during the frame without regard to the lane in which the second property occurred, while the other latch is selectable as an output latch from which the indication produced during the preceding frame is read.

4. The inspection system of claim 3 further comprising:
   a register arrangement for storing a first status signal representative of the application of a first characteristic signal to the serial memory selected during a frame as the input memory and a second status signal representative of the transmission of a signal out of that memory during the subsequent frame to provide a monitorable indication of the operability of that input memory.

5. The inspection system of claim 4 wherein
   the register arrangement is also adapted to store a third status signal representative of the application of a second characteristic signal to the latch selected during a frame as the input latch and a fourth status signal representative of the transmission of a signal out of that latch during the subsequent frame to provide a monitorable indication of the operability of the one latch.

6. The inspection system of claim 2 further comprising:
   a register arrangement for storing a first status signal representative of the application of a characteristic signal to the memory selected during a frame as the input memory and a second status signal representative of the transmission of a signal out of that memory during the subsequent frame to provide a monitorable indication of the operability of that input memory.

7. The inspection system of claim 1 further comprising:
   means operative during the first scan path in each frame for bypassing the logic network so that during that scan path the characteristic signal is applied to the input memory without passing through the logic network.

8. The inspection system of claim 1 wherein
   the discriminator is responsive to the pedestal signal to produce a second characteristic signal representative of a second predetermined physical property on the web, and further comprising:
   a first and second storage latch connected in parallel, one latch being selectable during alternate frames as an input latch for storing the second characteristic signal to provide an indication of the occurrence of the second property during the frame without regard to the lane in which the second property occurred, while the other latch is selectable as an output latch from which the indication produced during the preceding frame is read.

9. The inspection system of claim 8 further comprising:
   a register arrangement for storing a first status signal representative of the application of a first characteristic signal to the serial memory selected during a frame as the input memory and a second status signal representative of the transmission of a signal out of that memory during the subsequent frame to provide a monitorable indication of the operability of that input memory.

10. The inspection system of claim 9 wherein
    the register arrangement is also adapted to store a third status signal representative of the application of a second characteristic signal to the latch selected during a frame as the input latch and a fourth status signal representative of the transmission of a signal out of that latch during the subsequent frame to provide a monitorable indication of the operability of the one latch.

11. The inspection system of claim 1 further comprising:
    a register arrangement for storing a first status signal representative of the application of a characteristic signal to the memory selected during a frame as the input memory and a second status signal representative of the transmission of a signal out of that memory during the subsequent frame to provide a monitorable indication of the operability of that input memory.

12. A web inspection system for inspecting a web material that is subdivisible into a predetermined number of longitudinally extending frames comprising:

a source of radiation;

means for moving a spot of radiation transversely of the web along a plurality of generally parallel scan paths, each frame comprising a predetermined plurality of scan paths, each scan path being subdivisible into a predetermined plurality of transversely contiguous lanes;

a detector responsive to the radiation transmitted through or reflected by the web for generating an electrical pedestal signal representative thereof;

a discriminator network responsive to the pedestal signal for generating an electrical characteristic signal representative of the presence of a predetermined physical property on the web at a corresponding lane of the scan path;

first and second serial memories connected in parallel, each memory having a number of stages corresponding to the number of lanes; and a memory selector network for selecting during each frame one of the memories as an input memory and the other memory as an output memory so that during each frame each characteristic signal from the discriminator representing the presence of the predetermined physical property in a lane along each scan path is storable in the stage of the input memory corresponding to that lane to produce at the end of the frame an accumulated lane-by-lane summary of the occurrence of the predetermined physical property while, the other memory is selectable as an output memory from which the lane-by-lane summary produced during the preceding frame is read.

13. The web inspection system of claim 12 wherein the discriminator is responsive to the pedestal signal to produce a second characteristic signal representative of the presence of a second predetermined physical property on the web at a corresponding lane of the scan path; and wherein each memory has a memory bank corresponding to each physical property, each memory bank having a number of stages corresponding to the number of lanes; and wherein each characteristic signal representative of the first property and second property is storable in the corresponding bank at the stage therein corresponding to the lane in which each property occurred.

14. The web inspection system of claim 13 wherein each bank of each memory is connected in a recirculating configuration with the ouput of each memory bank being fed back to its input, the system further comprising:

a logic network connected intermediate the discriminator and the input to each bank of each memory, the logic network associated with the first bank deriving as its inputs the first characteristic signal and the memory signal recirculating from the first bank, the logic network associated with the second bank deriving as its inputs the second characteristic signal and the memory signal recirculating from the second bank to respectively apply to the input of each bank the logical sum of each pair of applied inputs.

15. The web inspection system of claim 14 further comprising means operative during the first scan path in each frame for bypassing the logic network so that during that scan path the first and second characteristic signals are applied to their respective banks of the input memory without passing through the associated logic network.

16. The web inspection system of claim 14 wherein the discriminator is responsive to the pedestal signal to produce a third characteristic signal representative of a third predetermined physical property on the web, and further comprising:

a first and a second storage latch connected in parallel, one latch being selectable during alternate frames as an input latch for storing the third characteristic signal to provide an indication of the occurrence of the third property during the frame without regard to the lane in which the third property occurred, while the other latch is selectable as an output from which the indication produced during the preceding frame is read.

17. The web inspection system of claim 16 further comprising:

a register arrangement for storing a first status signal representative of the application of a characteristic signal to the memory selected during a frame as an input memory and a second status signal representative of the transmission of a signal out of that memory during the subsequent frame to provide a monitorable indication of the operability of that input memory.

18. The web inspection system of claim 17 wherein the register arrangement is also adapted to store a third status signal representative of the application of a third characteristic signal to the latch selected during a frame as the input latch and a fourth status signal representative of the transmission of a signal out of that latch during the subsequent frame to provide a monitorable indication of the operability of the one latch.

19. The web inspection system of claim 13 wherein the discriminator is responsive to the pedestal signal to produce a third characteristic signal representative of a third predetermined physical property on the web, and further comprising:

a first and a second storage latch connected in parallel, one latch being selectable during alternate frames as an input latch for storing the third characteristic signal to provide an indication of the occurrence of the third property during the frame without regard to the lane in which the third property occurred, while the other latch is selectable as an output from which the indication produced during the preceding frame is read.

20. The web inspection system of claim 19 further comprising:

a register arrangement for storing a first status signal representative of the application of a characteristic signal to the memory selected during a frame as an input memory and a second status signal representative of the transmission of a signal out of that memory during the subsequent frame to provide a monitorable indication of the operability of that input memory.

21. The web inspection system of claim 20 wherein the register arrangement is also adapted to store a third signal representative of the application of a third characteristic signal to the latch selected during a frame as the input latch and a fourth status signal representative of the transmission of a signal out of that latch during the subsequent frame to provide a monitorable indication of the operability of the one latch.

22. The web inspection system of claim 12 wherein each memory is connected in a recirculating configuration with the memory output fed back to the input, the system further comprising:

a logic network connected intermediate the discriminator and the input to each of the memories, the logic network deriving as its inputs the characteristic signal generated during the current scan path and the recirculating memory signal to apply to the input memory the logical sum of these two inputs.

23. The web inspection system of claim 22 further comprising:

means operative during the first scan path in each frame for bypassing the logic network so that during that scan path the characteristic signal is applied to the input memory without passing through the logic network.

24. The web inspection system of claim 22 wherein the discriminator is responsive to the pedestal signal to produce a second characteristic signal representative of a second predetermined physical property on the web, and further comprising:

a first and a second storage latch connected in parallel, one latch being selectable during alternate frames as an input latch for storing the second characteristic signal to provide an indication of the occurrence of the second property during the frame without regard to the lane in which the second property occurred, while the other latch is selectable as an output latch from which the indication produced during the preceding frame is read.

25. The web inspection system of claim 24 further comprising:

a register arrangement for storing a first status signal representative of the application of a characteristic signal to the memory selected during a frame as an input memory and a second status signal representative of the transmission of a signal out of that memory during the subsequent frame to provide a monitorable indication of the operability of that input memory.

26. The web inspection system of claim 12 wherein the discriminator is responsive to the pedestal signal to produce a second characteristic signal representative of a second predetermined physical property on the web, and further comprising:

a first and a second storage latch connected in parallel, one latch being selectable during alternate frames as an input latch for storing the second characteristic signal to provide an indication of the occurrence of the second property during the frame without regard to the lane in which the second property occurred, while the other latch is selectable as an output latch from which the indication produced during the preceding frame is read.

27. The web inspection system of claim 26 further comprising:

a register arrangement for storing a first status signal representative of the application of a characteristic signal to the memory selected during a frame as an input memory and a second status signal representative of the transmission of a signal out of that memory during the subsequent frame to provide a monitorable indication of the operability of that input memory.

* * * * *